(12) United States Patent
Mitwally et al.

(10) Patent No.: US 8,685,950 B2
(45) Date of Patent: Apr. 1, 2014

(54) USE OF AROMATASE INHIBITORS FOR TREATMENT OF ECTOPIC PREGNANCY

(75) Inventors: Mohamed F. M. Mitwally, Bloomfield Hills, MI (US); Michael P. Diamond, Grosse Pointe Shores, MI (US); Robert F. Casper, Ontario (CA)

(73) Assignee: Wayne State University, Detroit, MI (US)

( * ) Notice: Subject to any disclaimer, the term of this patent is extended or adjusted under 35 U.S.C. 154(b) by 952 days.

(21) Appl. No.: 11/664,768

(22) PCT Filed: Oct. 4, 2005

(86) PCT No.: PCT/US2005/035864
§ 371 (c)(1),
(2), (4) Date: Apr. 4, 2007

(87) PCT Pub. No.: WO2006/041941
PCT Pub. Date: Apr. 20, 2006

(65) Prior Publication Data
US 2008/0025991 A1  Jan. 31, 2008

Related U.S. Application Data

(60) Provisional application No. 60/615,979, filed on Oct. 4, 2004.

(51) Int. Cl.
*A61K 31/56* (2006.01)
(52) U.S. Cl.
USPC .......................................................... 514/171
(58) Field of Classification Search
USPC .................................................. 514/171, 182
See application file for complete search history.

(56) References Cited

U.S. PATENT DOCUMENTS 4,888,331 A * 12/1989 Elger et al. .................... 514/170
5,583,128 A * 12/1996 Bhatnagar ..................... 514/177

OTHER PUBLICATIONS

Buzdar et al., Clinical Cancer Research,2001:7:2620-2635.*
Gazvani et al., Human Reproduction, 1998;13(7):1987-1990.*

* cited by examiner

*Primary Examiner* — San-Ming Hui
(74) *Attorney, Agent, or Firm* — Rohm & Monsanto, PLC

(57) ABSTRACT

Following a diagnosis of ectopic pregnancy, at least one aromatase inhibitor, is administered to a patient, either alone or in combination with other aromatase inhibitors or therapeutic agents or as an adjuvant to conservative surgical treatment, such as laparoscopy, to prevent the establishment and/or continuation of the ectopic pregnancy. In certain preferred embodiments, the aromatase inhibitor is administered in conjunction with methotrexate.

16 Claims, No Drawings

USE OF AROMATASE INHIBITORS FOR TREATMENT OF ECTOPIC PREGNANCY

CROSS-REFERENCE TO RELATED INVENTIONS

This application is a US national stage filing under 35 U.S.C. §371 of International Application No. PCT/US2005/035864 filed on Oct. 4, 2005, and claims the benefit under 35 U.S.C. §119(e) of, U.S. provisional application Ser. No. 60/615,979 filed on Oct. 4, 2004, the disclosure of which is incorporated herein by reference.

FIELD OF THE INVENTION

This invention relates to a method for medical treatment of ectopic pregnancy, and more specifically, to the administration of an aromatase inhibitor (AI) after ectopic pregnancy is diagnosed.

BACKGROUND OF THE INVENTION

Ectopic pregnancy, that is pregnancy outside the normal intrauterine implantation site, is a major cause of maternal morbidity and mortality. Ectopic pregnancy is occurring, with increasing incidence, worldwide. In the United States, for example, the annual incidence of ectopic pregnancy has increased more than five times, from 0.37% of pregnancies in 1948 to 1.97% in 1992. However, despite the continued rise in incidence, there was almost a 90% decline in the rate of death from ectopic pregnancy from 1979 to 1992. Nevertheless, ectopic pregnancy is still the third most common cause of maternal mortality in the United States, comprising about 9% of all such deaths. The most frequent direct causes of death are hemorrhage, infection, and anesthetic complications.

A number of factors have been implicated in the increased incidence of ectopic gestation, including pelvic inflammatory disease, complications of infections, the widespread clinical use of reconstructive tubal surgery, the widespread use of intrauterine devices, and the now widely practiced conservative surgical treatment of ectopic pregnancy itself.

The most important risk factor for ectopic pregnancy is a history of a previous ectopic gestation. This event confers a 10-fold increase in the likelihood of another ectopic pregnancy. Ectopic pregnancy occurs in as many as 10% of recipients of embryo transfer during in vitro fertilization. Indeed, the first pregnancy reported in humans with this technique was an ectopic pregnancy.

Of all ectopic pregnancies, 97% occur in the fallopian tube (tubal), 2.5% in the uterine cornu, and the remaining pregnancies occur in various other locations including the cervix, abdomen, and ovary. The majority of tubal pregnancies are located in the ampullary portion of the tube. Although interstitial and non-tubal ectopic pregnancies are rare, they account for about 20% of all fatalities.

Lawson Tait, the father of gynecologic surgery, reported the first successful operation, a salpingectomy by laparotomy, for ectopic pregnancy before the turn of this century. Until a little more than decade ago, however, little change had occurred in the diagnosis and management of ectopic pregnancy. The clinical use of sensitive pregnancy testing, ultrasonography, and diagnostic laparoscopy has had a major impact on the early diagnosis of this condition. The rate of ectopic rupture has therefore declined, and the option of conservative surgical management, by laparoscopy, of an unruptured fallopian tube is now a viable alternative.

Laparoscopic salpingostomy, although well-accepted as treatment for small-unruptured ectopic pregnancies, is still associated with high costs related to operating room expense, anesthesia services, and surgeons' fees. Conservative surgical options range from expression of a tubal abortion through the distal end of the tube to segmental resection and secondary anastomosis of an isthmic ectopic pregnancy. Any surgical therapy for ectopic pregnancy, however, may cause undesired postoperative adhesions due to surgical manipulation of the fallopian tubes. Of course, there remains an irreducible minimal degree of morbidity intrinsic to surgery and anesthesia.

The ultimate decision regarding surgical management depends on a patient's desire for future fertility. If a patient is not interested in future fertility, the appropriate surgical procedure is salpingectomy. If a patient does desire future fertility, however, much data from the past few years support performing conservative surgery in a majority of these cases. Irrespective of the surgical procedure performed, the pregnancy rate after an ectopic pregnancy is decreased by 40% to 70%. There is a need, therefore, for non-surgical approaches to the management and care of ectopic pregnancy in order to overcome the costs and risks attendant to surgery.

Non-surgical techniques for managing ectopic pregnancy include hospitalization for observation/expectant care or medical management of ectopic pregnancy with a drug, such as methotrexate. Observation/expectant care involves a rigid and expensive hospital protocol that includes serial ultrasound examinations and serum chorionic gonadotropin (hCG) measurements to observe whether the ectopic pregnancy will undergo spontaneous absorption and, therefore, require no surgical or medical intervention. If the pregnancy spontaneously resolves, this technique results in a better rates of subsequent pregnancy than that achieved by removing the ectopic pregnancy by salpingostomy at a first diagnostic laparoscopy. At present, the consensus is that it is better to remove an unruptured ectopic pregnancy at the time of first laparoscopy to avoid the additional expense of hospitalization, serial hCG assays, and a second laparoscopy. At this time, expectant management is considered an option only for patients with extreme surgical risk, falling hCG titers, or in a research setting.

Ectopic pregnancy has been treated with a variety of agents, with varying degrees of success, including methotrexate, prostaglandins, dactinomycin, etoposide, hyperosmolar glucose, anti-hCG antibodies, potassium chloride, and mifepristone (RU 486). Although systemic treatments are the most practical, several of these agents also have been injected locally into the ectopic gestational sac under laparoscopic or ultrasound guidance or by hysteroscopic intratubal cannulation.

At this time, parenteral methotrexate seems to be the best-studied and most accepted agent for the medical treatment of ectopic pregnancy. Methotrexate, a folic acid antagonist, inhibits dihydrofolate reductase, an enzyme necessary for nucleic acid synthesis, and thereby interferes with DNA synthesis and cell multiplication in actively dividing tissue. The efficacy of methotrexate in the treatment of gestational trophoblastic disease made it an attractive candidate for chemotherapeutic use in ectopic pregnancy, including use as an adjuvant to conservative surgery to treat persistent ectopic pregnancy.

However there are several problems associated with methotrexate therapy including serious side effects, contraindications in certain medical conditions, and high failure rates when there are high levels of $\beta$-hCG (>10,000 IU/ml) and progesterone (>10 ng/ml). Systemic methotrexate therapy is contraindicated in patients who are hemodynamically unstable or have signs of bone marrow depression or liver or renal dysfunction, as evidenced by leukopenia and/or thrombocytopenia, elevated liver enzymes, or elevated serum creatinine, respectively.

Most notably, however, there is a significantly long period to resolution of the pregnancy (more than three weeks in most patients) with the occasional need for repeat administration of methotrexate that accounts for most of the cost of the medical treatment due to the long follow-up period. In addition to the obvious impact on the cost of treatment, the prolonged follow-up period associated with methotrexate treatment has been found to have an adverse impact on the patients' quality of life, including causing depression.

Thus, there remains a need for a medication that overcomes the shortcomings of methotrexate, or that can add to the efficacy of methotrexate treatment of ectopic pregnancy by increasing the success rate, especially in patients with initial high β-hCG and progesterone levels, and that can shorten the interval to recovery, which would reduce the cost of treatment and improve the quality of life of the patients.

To establish and successfully maintain a human pregnancy requires the coordinated secretion of hormones within and between the fetus, mother, and placenta. The placenta synthesizes and secretes steroid and peptide hormones that regulate hormonogenesis by endocrine glands in both the mother and the fetus. Placental hormones also act in a paracrine and/or autocrine manner to regulate growth and differentiation of placental cytotrophoblast and syncytiotrophoblast, growth and maturation of the placental vascular tree, and uterine endovascular invasion by extravillous cytotrophoblast. Moreover, the placenta metabolizes the large quantities of steroid hormones produced by the maternal endocrine glands to protect the fetus and to orchestrate the timing and development of fetal organ systems, the fetal pituitary-adrenocortical axis in particular. Clearly, placental hormonogenesis and metabolism are among the most important determinants of a successful pregnancy.

The role of estrogen in the establishment and maintenance of early pregnancy is controversial. Studies have that found that progesterone only was needed to rescue pregnancy after corpus luteum removal without the need for a concomitant estrogen administration. Ghosh, et al. Luteal phase ovarian oestrogen is not essential for implantation and maintenance of pregnancy from surrogate embryo transfer in the rhesus monkey, *Hum. Reprod.*, Vol. 9, No. 4, pages 629-37 (1994). Successful pregnancies have been found in conditions associated with very low estrogen levels such as aromatase deficiency. Morishima, et al., Aromatase deficiency in male and female siblings caused by a novel mutation and the physiological role of estrogens, *J. Clin. Endocrinol. Metab.*, Vol. 80, page 3689 (1995); France, Steroid sulfatase deficiency, *J. Steroid Biochem.*, Vol. 11, page 647 (1979); and Shozu, et al., A new cause of female pseudohermaphroditism: Placental aromatase deficiency, *J. Clin. Endocrinol. Metab.*, Vol. 72, page 560 (1991). Moreover, there has been a failure to consistently demonstrate estrogen receptors in the trophoblast and early pregnancy placenta. Rossmanith, et al., The demonstration of progesterone, but not of estrogen, receptors in the developing human placenta. *Horm. Metab. Res.*, Vol. 29, No. 12, pages 604-610 (1997).

Nevertheless, we believe that estrogen plays a pivotal role in the establishment and maintenance of early pregnancy and that disruption of estrogen formation and/or function would result in the failure of early pregnancy leading to pregnancy loss. we believe that the findings contrary to the role of estrogen in establishing and maintaining pregnancy can be refuted.

It is known that the corpus luteum is the main source of estrogen and progesterone in early pregnancy until the establishment of the placenta. In their experiments, Ghosh, et al. found progesterone supplementation only (without estrogen) to be necessary for the maintenance of pregnancy after removal of the corpus luteum. However, they did not consider the non-corpus luteum sources of estrogen production, i.e., the embryo as well as the early developing placenta. We believe that estrogen plays its role in early pregnancy, indirectly, by two mechanisms: the first through priming for progesterone action by upregulating progesterone receptors, and the second by enhancing progesterone production by the placenta and corpus luteum through various mechanisms including increase in receptor-mediated LDL uptake and LDL receptor and P450scc (128) mRNA expression in placental trophoblasts.

In brief, it seems that the role of estrogen in maintaining early pregnancy is mediated by progesterone. Hence, it is obvious that administering progesterone alone would be enough to rescue pregnancy after corpus luteum removal without the need for estrogen administration. Moreover, estrogen administration alone would not result in maintenance of pregnancy after removal of the corpus luteum, due to the absence of the main machinery for the production of progesterone at that stage of pregnancy. Another important point not to be missed is the theoretical possibility of conversion of administered progesterone to estrogens but not the reverse. Looking at the steroidogenesis cascade, estrogens are terminal products while progesterone is an early product in the steroidogenesis cascade.

Although pregnancy is maintained in most women having low estrogen levels resulting from deficiencies in various placental enzymes, it is interesting to note that, although maternal estradiol levels are markedly reduced, concentrations are found to be close to 0.45 ng/mL, or $10^{-9}$ mol/L, a concentration that approximates the dissociation constant for estradiol binding to its receptor. Differences in the outcome of pregnancy in various women with estrogen deficiency suggest that the important biologic effects of estradiol can be achieved with available receptor and concentrations of estrogen sufficient to interact with it. It would appear that in both human and nonhuman primate pregnancy, estrogen is produced in considerable excess. In the baboon, when two estrogen antagonists were administered in early pregnancy to study the effect of estrogen deprivation on progesterone production, a depression in plasma progesterone indicating a placental requirement for estrogen in progesterone product was found with the pure estrogen antagonist, MER-25, while with the other antagonist, trioxifene mesylate, no such effect was found apparently due to an inherent estrogenicity of trioxifene. This would indicate that even such minimal estrogenic activity is still enough to exert its role in early pregnancy.

Moreover, in females with aromatase deficiency, the placenta would be unaffected because it would still carry a complement of genes from the father as well, and therefore, would produce estrogen.

Despite their failure to detect the estrogen receptor in the human trophoblast, Rossmanith, et al. concluded that their finding does not entirely preclude the presence of this receptor in human trophoblasts, but might be attributed to a relatively low number and density of estrogen receptors on these cells. Alternatively, a different type of estrogen receptor may mediate estrogen action on the placenta, such as by a non-classical membrane-bound receptor. Most recently, Bukovsky, et al., Expression and localization of estrogen receptor-alpha protein in normal and abnormal term placentae and stimulation of trophoblast differentiation by estradiol, *Reprod. Biol. Endocrinol.*, Vol. 6, No. 1, page 12 (2003), reported the expression and localization of estrogen receptor-alpha protein in normal and abnormal term placentae and stimulation of trophoblast differentiation by estradiol.

In addition to debunking the evidence contrary to the role of estrogen, we have become convinced that estrogen plays a pivotal role in the establishment and maintenance of pregnancy based on, inter alia, on the following four facts:

First: Existence of Estrogen Synthase Enzyme (Aromatase and 17HSD1) and Estrogen Production by the Corpus Luteum, Embryo and Trophoblast. Normal Estrogen Production is Associated with Healthy Development of Early Pregnancy.

The human placenta is a unique organ for the maintenance of pregnancy. Its important functions include hormone supply for the maternal body and fetal development. In addition to the synthesis of placenta-specific hormones, such as human chorionic gonadotropin and placental lactogen, the placenta plays a critical role in producing progesterone and estrogens throughout gestation). Trophoblast cells secrete progesterone; the production of which can be doubled in vitro in the presence of pure hCG.

Both P450arom and 17HSD1 are abundantly expressed in syncytiotrophoblast cells, in line with the role of syncytiotrophoblast cells in endocrine function. Cytosolic 17HSD1 has been found in the nuclei of syncytiotrophoblast. Cultured cytotrophoblast cells purified from first-trimester placenta express both P450arom and 17HSD1 and are capable of converting dehydroepiandrosterone and A-dione to $E_2$.

During human pregnancy, the production of 17-β-estradiol rises eighty fold, from 0.75 nM preovulatory peak to 60 nM at term), and estrogens influence various aspects of placental function and fetal development in humans and primates. The corpus luteum is the main source of estrogen and progesterone during early stages of pregnancy during which, hCG is responsible for corpus luteum hormonal rescue and maintenance of luteal estradiol and progesterone production. Estradiol has been found also to be produced from embryonic and endometrial sources suggesting a permissive role in embryo implantation. In addition, the blastocyst actively participates in the process of implantation. Mechanisms that enable the blastocyst to initiate implantation (a process termed activation) include catecholestrogens, a class of estrogen metabolites.

Most recently, Li, et al., Expression of P450 aromatase and 17-β-hydroxysteroid dehydrogenase type 1 at fetal-maternal interface during tubal pregnancy, *J. Steroid Biochem. Mol. Biol.*, Vol. 87(4-5), pages 241-6 (2003), studied the expression pattern of P450arom and 17HSD1 at the fetal-maternal interface, particularly in various trophoblast cells, in tubal pregnancy. Using in situ hybridization, P450arom mRNA was localized in syncytiotrophoblast cells, which are mainly responsible for hormone production during pregnancy. In addition, 17HSD1 was found in epithelial cells of the fallopian tube. Interestingly, the Li, et al. found that the expression level of 17HSD1 in fallopian tube epithelium during tubal pregnancy was significantly higher than that during normal cycle. This study provided the first evidence that normal and tubal pregnancies possess identical expression of P450arom and 17HSD1 in syncytiotrophoblast cells and therefore, similar estradiol production in the placenta. The authors suggested that the association of 17HSD1 with extravillous cytotrophoblast cells indicates that 17HSD1 perhaps play a role in trophoblast invasion. Moreover, increased expression of 17HSD1 in epithelial cells of fallopian tube may lead to a local estradiol supply sufficient for the maintenance of tubal pregnancy.

Estradiol levels are known to be low in abnormal pregnancies including ectopic pregnancy and abortion. In women with threatened first-trimester abortion, abnormal estradiol concentrations are highly associated with a subsequent pregnancy loss. Nygren, et al., Evaluation of the prognosis of threatened abortion from the peripheral plasma levels of progesterone, estradiol and human chorionic gonadotropin, *Am. J. Obstet. Gynecol.*, Vol. 116, page 916 (1973).

The fall in estradiol concentrations was seen in ectopic pregnancies with an abnormal doubling time for HCG and in all abortions. When the ectopic pregnancy had a normal doubling time, estradiol and progesterone concentrations were normal. These findings suggest that corpus luteum function particularly in ectopic pregnancy depends on an adequate doubling time of HCG more than an absolute value, and with normal trophoblastic tissue the site of implantation does not affect corpus luteum function. In abortions, the fall in estradiol and progesterone concentrations was less influenced by the doubling time of HCG. Alam, et al. Preliminary results on the role of embryonic human chorionic gonadotrophin in corpus luteum rescue during early pregnancy and the relationship to abortion and ectopic pregnancy, *Hum. Reprod.* Vol. 14, No. 9, pages 2375-8 (1999). These findings suggest that the function of the corpus luteum in ectopic pregnancy is expected to be defective due to the lower levels of hCG produced in ectopic pregnancy which indicates a crucial role for steroidogenesis by the developing trophoblast in maintaining ectopic pregnancy.

Second: Presence of Estrogen Receptors in the Trophoblastic Tissues Mediating Its Actions on Trophoblastic Differentiation and Invasion Several studies have shown that human placenta binds estradiol. However, more recent immunohistochemical studies on paraffin-embedded or snap frozen sections as well as other techniques (RT-PCR for ER-α mRNA) failed to demonstrate estrogen receptor α in human placentae during pregnancy or in cultures of dispersed placental cells. However, the failure to detect the estrogen receptor α (ERα) does not entirely preclude the presence of this receptor in human trophoblast cells, but rather might be attributed to a relatively low number and density of the receptor on these cells. There have been reports of identification of the estrogen receptor a in the nuclei of cultured human placental syncytiotrophoblast. None of the above mentioned studies applied western blot analysis of placental ERα expression until recently when Bukovsky, et al., using western blot analysis, found that in normal placentae, nuclear estrogen receptor α expression was confined to villous cytotrophoblast cells. In abnormal placentae, they found no cytotrophoblast expressing ERα was detected. The authors concluded that placental ERα expression in vivo is high in normal placentae and barely detectable in abnormal placentae. The significant increase of estrogen production occurring with pregnancy advancement may play a role, via the ERα, in the stimulation of terminal differentiation of mononucleated trophoblast cells into syncytial aggregates and in promoting placental function. This mechanism, however, may not operate in abnormal placentae, which show a lack of ERα expression Third: Significant Role of Estrogen in Progesterone Action through Both an Effect on Progesterone Receptors Upregulation and an Effect on Progesterone Production Early in Pregnancy Estrogen and progesterone play pivotal roles during the implantation process and the establishment and maintenance of pregnancy. Progesterone, which is secreted initially by the corpus luteum and later by the placenta, is essential in maintaining an ongoing pregnancy. Ghost, Another look at the issue of peri-implantation oestrogen, *Hum. Reprod.*, Vol. 10, pages 1-2 (1995). Without progesterone support, the embryo is expelled by a prostaglandin-mediated mechanism. Clinically, preventing the synthesis of progesterone, or blocking its action at the receptor, can accomplish inhibition of progesterone effects. Epostane, a 3β-hydroxysteroid dehydrogenase inhibitor, prevents synthesis of progesterone, and has been investigated for terminating pregnancy, but requires dosing every 6 hours for 7 days in order to effect abortion.

Estrogenic and progestational actions on target cells are mediated through estrogen receptors and progesterone receptors, respectively. Both progesterone and estrogen receptors are members of the steroid-retinoid receptor superfamily, and function as steroid-modulated transcription factors.

The levels of progesterone receptor and estrogen receptors are thought to be critical in determining cell responsiveness to steroids, and thus receptor regulation has been studied extensively. Progesterone receptor is one of most well-documented, estrogen-regulated genes. In many target tissues, both normal and neoplastic, progesterone receptor is induced by estrogen and is widely recognized as a marker for estrogen action.

In vitro studies have shown that human, rat and rabbit progesterone receptors are induced through binding of the occupied estrogen receptor to multiple estrogen-responsive regions in the 5'-region of progesterone receptor gene. In many species, estrogen up-regulates progesterone receptor in almost all uterine cell types including the epithelium. These reports are consistent with a model of estrogen regulation of progesterone receptor in which occupied estrogen receptor binds to the progesterone receptor promoter and activates transcription of the progesterone receptor gene.

The expression of progesterone receptor, and therefore sensitivity to progestins, is under the control of estrogen, which increases, and progesterone, which decreases progesterone receptor expression in most target tissues. Progesterone receptor protein is increased during proestrus or by exogenous estrogen administration in the mammalian uterus.

It is well known that estradiol increases the concentration of its own receptor as well as that of progesterone receptor in normal endometrium at the same time progesterone, in adequate amounts, counteracts these estrogenic effects. Moreover, unoccupied progesterone receptor also plays a role in the control of progesterone receptor biosynthesis in primate endometrium as suggested by Chwalisz, et al., Inhibition of the oestradiol mediated endometrial gland formation by the antigestagen onapristone in rabbits: relationship to uterine estrogen receptor, *Endocrinology*, Vol. 129, pages 312-2 (1991). Anti-estrogen also counteracts such estrogenic effects/action. Treatment with anti-estrogen CDRI-85/287 was found to decrease the amount of both receptors suggesting that anti-estrogens may have decidualization inhibitory activity in primate endometrium.

Estrogen has been shown to play an important role in progesterone production by the trophoblast. During rat and rabbit pregnancy, estrogen is the major luteotropic stimulus that maintains the corpus luteum and progesterone production. Estrogen stimulates the uptake of high-density lipoprotein cholesterol substrate and P450scc expression in the rat and rabbit corpus luteum, thereby promoting progesterone production. During mid- to late primate pregnancy, when the placenta is the principal source of progesterone, estrogen has a similar regulatory role within trophoblasts. Placental progesterone formation and serum progesterone concentrations are decreased by administration of the estrogen receptor antagonist ethamoxytriphetol in baboons, an effect that can be reversed by diethylstilbestrol. Moreover, placental progesterone production by human trophoblasts in culture is inhibited by treatment with an aromatase inhibitor and restored by estradiol. The increase in receptor-mediated LDL uptake and LDL receptor and P450scc mRNA expression in placental trophoblasts observed during the second half of baboon pregnancy when estrogen levels rise, can be suppressed by blocking the action or formation of estrogen. In contrast, placental 3β-HSD and adrenodoxin mRNA expression and 3β-HSD activity are not developmentally regulated or altered by anti-estrogen treatment in baboons. Therefore, inhibiting the action or levels of estrogen specifically blocks the developmental increase in placental LDL cholesterol uptake and expression of the P450scc enzyme essential for the metabolism of cholesterol to pregnenolone in baboons.

Fourth: Disruption of Estrogen Function is Associated with Defective Early Pregnancy Development Strong evidence is accumulating to support the crucial role of estrogen in the establishment and maintenance of early pregnancy. A 50% spontaneous abortion rate has been observed among women having a mutation in the amino terminal region of the estrogen receptor involved in transcription. Lehrer, et al., Oestrogen receptor B-region polymorphism and spontaneous abortion in women with breast cancer. *Lancet*, Vol 335, page 622 (1990). In the baboon, reduction of maternal estrogen levels to less than 0.1 ng/mL by daily administration of an inhibitor of placental estrogen synthesis resulted in a 66% incidence of abortion during early gestation that was prevented by treatment with exogenous estradiol. Albrecht, et al., The role of estrogen in the maintenance of primate pregnancy, *Am. J. Obstet. Gynecol.*, Vol. 182, page 432 (2000). Derfoul, et al., Estrogenic endocrine disruptive components interfere with calcium handling and differentiation of human trophoblast cells, J. Cell Biochem., Vol. 89, No. 4, pages 755-770 (2003). suggested that trophoblast $Ca^+$ handling functions are endocrinally modulated, and that their alteration by estrogen disruptors constitutes a possible pathway of the harmful effects on fetal development.

If estrogen does in fact play a significant role in establishing and maintaining early pregnancy, then disruption of estrogen formation and/or function would result in the failure of early pregnancy leading to pregnancy loss.

Although most of the data used by the inventors to come to conclusion that the estrogen has a major role in the establishment and maintenance of early pregnancy comes from studies involving intrauterine pregnancy. We have come to the conclusion that there are similarities between intra- and extrauterine pregnancy in regard to steroidogenesis and comparable roles for estrogen and progesterone in the support of early pregnancy phase. Extrapolation of these data from intrauterine pregnancy towards ectopic pregnancy is supported by the available data on placentation in ectopic pregnancy (Randall, et al., Placentation in the fallopian tube. *Int J Gynecol Pathol.*, Vol. 6, No. 2. pages 132-9 (1987)); as well as recent data on steroidogenesis in ectopic pregnancy (see, Li, et al., Expression of P450 aromatase and 17 β-hydroxysteroid dehydrogenase type 1 at fetal-maternal interface during tubal pregnancy, *J Steroid Biochem Mol. Biol.*, Vol. 87(4-S), pages 241-6 (2003) and apopotosis in extravillous trophoblast cells (von Rango, et al., Apoptosis of extravillous trophoblast cells limits the trophoblast invasion in uterine but not in tubal pregnancy during first trimester, *Placenta*, Vol. 24, No. 10, pages 929-40 (2003).

Aromatase is a microsomal member of the cytochrome P450 hemoprotein-containing enzyme complex superfamily (P450arom, the product of the CYP19 gene) that catalyzes the rate-limiting step in the production of estrogens, that is, the conversion of androstenedione and testosterone via three hydroxylation steps to estrone and estradiol respectively. Aromatase activity is present in many tissues, such as the ovaries, the brain, adipose tissue, muscle, liver, breast tissue, and in malignant breast tumors. The main sources of circulating estrogens are the ovaries in premenopausal women and adipose tissue in postmenopausal women.

Aromatase is a good target for selective inhibition because estrogen production is a terminal step in the biosynthetic sequence. A large number of aromatase inhibitors have been developed and utilized in clinical studies over the last 20 years, mainly for treatment of breast cancer.

The first aromatase inhibitor to be used clinically was aminoglutethimide, which induces a medical adrenalectomy by inhibiting many other enzymes involved in steroid biosynthesis. Although aminoglutethimide is an effective hormonal agent in postmenopausal breast cancer, its use is complicated by the need for concurrent corticosteroid replacement. In addition side effects, like lethargy, rashes, nausea and fever, result in 8-15% of patients stopping the aminioglutethimide treatment. The lack of specificity and unfavorable toxicity profile of aminoglutethimide has led to a search for more specific aromatase inhibitors. In addition, the earlier aromatase inhibitors were not able to completely inhibit aromatase activity in premenopausal patients. Therefore, aromatase inhibitors have been primarily used for postmenopausal patients.

Due to the controversy over the role of estrogen, inter alia, aromatase inhibitors have not heretofore been used for prevention of the establishment and/or continuation of an ectopic pregnancy, or for medical termination of pregnancy. In fact, aromatase inhibitors have recently been used in assisted reproductive techniques, such as in vitro fertilization (IVF), Gamete Intrafallopian Transfer Procedure (GIFT), Zygote Intrafallopian Transfer Procedure (ZIFT), Intracytoplasmic Sperm Injection (ICSI), Intrauterine Insemination (MUM), Therapeutic Donor Insemination (TDI) and Controlled Ovarian Hyperstimulation (COH) to improve the implantation and/or pregnancy rate.

Aromatase inhibitors have been classified in a number of different ways, including first-, second-, and third-generation; steroidal and nonsteroidal; and by binding activity, i.e., reversible (ionic binding) and irreversible (suicide inhibitor, covalent binding). The most successful, third generation aromatase inhibitors are now available commercially for breast cancer treatment.

The commercially available agents include two nonsteroidal preparations, anastrozole and letrozole, and a steroidal agent, exemestane. Exemstane is available from Pfizer Inc., New York, N.Y. under the trademark Aromasin®; Anastrozole, is available from AstraZeneca under the trademark Arimidex® (ZN 1033); and letrozole is available from Novartis Pharmaceutical Corporation under the trademark Femara® CGS 20267). Anastrozole and letrozole are selective aromatase inhibitors, available for clinical use in North America, Europe and other parts of the world for treatment of postmenopausal breast cancer. These triazole (antifungal) derivatives are reversible, competitive aromatase inhibitors, which are highly potent and selective. Their intrinsic potency is considerably greater than that of aminoglutethimide, and at doses of 1-5 mg/day, they inhibit estrogen levels by 97% to >99%. This level of aromatase inhibition results in estradiol concentrations below detection by most sensitive immunoassays. The high affinity of aromatase inhibitors for aromatase is thought to reside in the −4 nitrogen of the triazole ring that coordinates with the heme iron atom of the aromatase enzyme complex. Aromatase inhibitors are completely absorbed after oral administration with mean terminal $t_{1/2}$ of approximately 45 hr (range, 30-60 hr). They are cleared from the systemic circulation mainly by the liver. Gastrointestinal disturbances account for most of the adverse events, although these have seldom limited therapy. Other adverse effects are asthenia, hot flashes, headache, and back pain.

SUMMARY OF THE PRESENT INVENTION

The present invention involves the use of an aromatase inhibitor, alone or in combination with other aromatase inhibitors and/or other medications, including but not exclusive to methotrexate, for treatment of ectopic pregnancy, and more specifically for prevention of the establishment and/or continuation of an ectopic pregnancy.

In a method embodiment, the ectopic pregnancy is first diagnosed by techniques known in the art. Patients clinically suspected of having ectopic pregnancy fall into two major categories: those who have an acute abdomen and in whom immediate surgery is indicated, and those who are clinically stable and in whom adjunctive diagnostic procedures can be performed. The modern approach to the evaluation of clinically stable patients suspected of having an ectopic pregnancy is based on the combined use of sensitive pregnancy testing (or hCG testing), abdominal or transvaginal ultrasound examination, and diagnostic laparoscopy. The hCG test is used to screen for pregnancy, and ultrasonography is employed to locate it. In acute cases, a rapid urine pregnancy test and a culdocentesis may be employed. A positive culdocentesis in a patient with a positive pregnancy test result has been reported to correspond with ectopic pregnancy in 99.2% of cases.

The administration of the aromatase inhibitor, alone or in combination with other medication(s), may be given as a single dose for one day or multiple days, or as multiple doses for one day or multiple days. Other medications may be started before, concurrent with, or subsequent to starting the administration of the aromatase inhibitor(s).

Administration of the aromatase inhibitor(s) alone, or in conjunction with other medications, can start immediately after the diagnosis of ectopic pregnancy, or can be started several days after conservative management or can be started concomitantly with surgical management as an adjuvant therapy. As used herein, the term "conservative management" includes surgical techniques, such as the well-known laparoscopic techniques currently employed to treat ectopic pregnancies.

The administration of the aromatase inhibitor(s) alone or in combination together, or in conjunction with other medications or other therapies, can be done orally, parenterally or through other known routes of pharmacologic administration of medications such as but not exclusive to transvaginal and transrectal routes of administration, and through the skin or mucous membranes. Oral administration is, of course, the preferred route.

Although not wishing to be bound by theory, there are several possible mechanisms that explain the success of aromatase inhibitors in preventing establishment and/or the continuation of pregnancy. The main hypothesis is the prevention of the establishment of early ectopic pregnancy by inducing atrophy and death of the trophoblastic tissues secondary to estrogen deprivation leading to inhibition of progesterone action. Both estrogen and progesterone are necessary for the maintenance of pregnancy. Progesterone receptors are dependant on estrogen priming. Moreover, estrogen is required to enhance progesterone production during pregnancy. We hypothesize that the use of an aromatase inhibitor results in suppression of estrogen production leading to estrogen deprivation, which will interfere with progesterone action indirectly through suppression of progesterone receptors as a result of estrogen depletion, as well as suppression of progesterone production. Thus, we propose that the prevention of the establishment of ectopic pregnancy and destruction of the early trophoblastic tissue by aromatase inhibition is the result of two mechanisms: first, a direct mechanism involving local estrogen withdrawal by inhibition of blastocyst and trophoblastic aromatase and local estrogen production, and second, by a direct or indirect intraovarian effect resulting from steroid precursor substrate failure (i.e., androgens and progestins) to be converted to estrogens by reduced aromatase levels induced by the AI resulting in a drop in circulating estrogen levels.

Both "estrogen withdrawal" actions are expected to result in a cascade of events resulting in the disruption of trophoblastic integrity leading to its breakdown and the induction of ectopic pregnancy atrophy and destruction. Therefore, trophoblastic disruption will occur, regardless of the gestational age of the ectopic pregnancy in which the aromatase inhibitor is given. Thus, the present invention provides a method for preventing the establishment and/or maintenance of ectopic pregnancy in females by oral administration of an aromatase inhibitor and the consequent blockade of estrogen synthesis.

The use of an aromatase inhibitor alone may be an effective alternative modality for medical management of ectopic pregnancy. This has the advantages of significantly higher safety as well as less cost, and the convenience of oral administration. In another embodiment, administering an aromatase inhibitor in conjunction with methotrexate therapy would improve the outcome of methotrexate treatment, which is presently the current standard for medical management of ectopic pregnancy. By improved outcome we mean that there would be a lower failure rate of treatment, a decrease in the need for a repeat second or more doses of methotrexate, a shortened interval between initiation of treatment and the complete resolution (negative serum β-hCG levels). Further, a lower dose of methotrexate would be required for achieving complete resolution of the pregnancy, and consequently the adverse side effects of methotrexate would be lessened.

Other significant advantages include the excellent safety profile of third generation aromatase inhibitors and their high tolerability. Specifically, third generation aromatase inhibitors lack the significant contraindications that have limited the success, or even the use of, methotrexate in some women with medical contraindications.

In addition, the third generation aromatase inhibitors are administered orally without known significant allergic reactions, drug interactions or contraindications. The use of the aromatase inhibitors, therefore, would reduce significantly the cost of medical treatment of ectopic pregnancy, reduce the interval to compete resolution, and shorten the follow-up period, as well as reducing the failure rate of the currently available medical treatment. This would also have a significant positive impact on the quality of life for patients with ectopic pregnancy.

While a single aromatase inhibitor is preferred for use in the present invention, combinations of aromatase inhibitors, and especially those aromatase inhibitors having different half-lives, are within the contemplation of the invention. The aromatase inhibitor is preferably selected from aromatase inhibitors having a half-life of about 8 hours to about 4 days, more preferably from aromatase inhibitors having a half-life of about 2 days. Most beneficial are those aromatase inhibitors selected from non-steroidal and reversible aromatase inhibitors. More details on the types of aromatase inhibitors that may be used in the methods, uses and preparations of the present invention appear subsequently herein.

The aromatase inhibitors that have been found to be most useful of the commercially available forms are those in oral form. This form offers clear advantages over other forms, including convenience and patient compliance. Preferred aromatase inhibitors of those that are presently commercially available, include anastrozole, letrozole, vorozole and exemestane. Exemestane (Aromasin™) is an example of a steroidal, non-reversible aromatase inhibitor that is specifically contemplated for use in the present invention.

The daily doses required for the present invention depend on the type of aromatase inhibitor that is selected for use. Some inhibitors are more active than others, and hence, lower amounts of the former inhibitors could be used.

Examples of preferred dosages are as follows. When the aromatase inhibitor is letrozole, it is preferably administered in a daily dose of from about 2.5 mg to about 30 mg. When the aromatase inhibitor is anastrozole, preferably, it is administered in a daily dose of from about 1 mg to about 30 mg. When the aromatase inhibitor is vorozole, the preferred daily dose is from about 4 to about 30 mg. Exemestane is preferably administered in a daily dose of about 25 to 200 mg. Preferred are 1 to 10 daily doses of the aromatase inhibitor, and most preferably the daily doses of the aromatase inhibitor comprise five daily doses.

In a particularly preferred form of the invention, a single dose of AI is administered in place of the multiple daily doses described above. The aromatase inhibitor is preferably administered in a single dose selected from amounts in the range of, for example, from about 5 mg to 60 mg of letrozole or arimidex to about 500 to 2000 mg of exemestane. The amount of AI administered should be effective to induce ectopic pregnancy atrophy and destruction.

As used herein, the term "aromatase inhibitors" is to be understood as substances that inhibit the enzyme aromatase (=estrogen synthetase), which is responsible for converting androgens to oestrogens.

Aromatase inhibitors may have a non-steroidal or a steroidal chemical structure. According to the present invention, both non-steroidal aromatase inhibitors and steroidal aromatase inhibitors can be used.

By "aromatase inhibitors" there are to be understood especially those substances that in a determination of the in vitro inhibition of aromatase activity exhibit $IC_{50}$ values of $10^{-5}$ M or lower, especially $10^{-6}$ M or lower, preferably $10^{-7}$ M or lower and most especially $10^{-8}$ M or lower.

The in vitro inhibition of aromatase activity can be demonstrated, for example, by using the methods described in *J. Biol. Chem.*, Vol. 249, page 5364 (1974) or in *J. Enzyme Inhib.*, Vol. 4, page 169 (1990). In addition, $IC_{50}$ values for aromatase inhibition can be obtained, for example, in vitro by a direct product isolation method relating to inhibition of the conversion of 4-$^{14}$C-androstenedione to 4-$^{14}$C-oestrone in human placental microsomes.

By "aromatase inhibitors" there are to be understood most especially substances for which the minimum effective dose in the case of in vivo aromatase inhibition is 10 mg/kg or less, especially 1 mg/kg or less, preferably 0.1 mg/kg or less and most especially 0.01 mg/kg or less.

In vivo aromatase inhibition can be determined, for example, by the following method as described in *J Enzyme Inhib.*, Vol. 4, page 179 (1990:

Androstenedione (30 mg/kg subcutaneously) is administered on its own or together with an aromatase inhibitor (orally or subcutaneously) to sexually immature female rats for a period of 4 days. After the fourth administration, the rats are sacrificed and the uteri are isolated and weighed. The aromatase inhibition is determined by the extent to which the hypertrophy of the uterus induced by the administration of androstenedione alone is suppressed or reduced by the simultaneous administration of the aromatase inhibitor.

The following groups of compounds are listed as examples of aromatase inhibitors. Each individual group forms a group of aromatase inhibitors that can be used successfully in accordance with the present invention:

(a) The compounds of formulae I and I* as defined in European Patent Publication No. EP-A-165 904. These are especially the compounds of Formula I

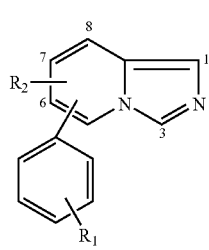

(I)

wherein $R_1$ is hydrogen, lower alkyl; lower alkyl substituted by hydroxy, lower alkoxy, lower alkanoyloxy, lower alkanoyl, amino, lower alkylamino, di-lower alkylamino, halogen, sulfo, carboxy, lower alkoxycarbonyl, carbamoyl or by cyano; nitro, halogen, hydroxy, lower alkoxy, lower alkanoyloxy, phenylsulfonyloxy, lower alkylsulfonyloxy, mercapto, lower alkylthio, lower alkylsulfinyl, lower alkylsulfonyl, lower alkanoylthio, amino, lower alkylamino, di-lower alkylamino, lower alkyleneamino, N-morpholino, -thiomorpholino, N-piperazino that is unsubstituted or lower alkyl-substituted in the 4-position, tri-lower alkylammonio, sulfo, lower alkoxysulfonyl, sulfamoyl, lower alkylsulfamoyl, di-lower alkylsulfamoyl, formyl; iminomethyl that is unsubstituted or substituted at the nitrogen atom by hydroxy, lower alkoxy, lower alkanoyloxy, lower alkyl, phenyl or by amino; $C_2$-$C_7$ alkanoyl, benzoyl, carboxy, lower alkoxycarbonyl, carbamoyl, lower alkylcarbamoyl, di-lower alkylcarbamoyl, cyano, 5-tetrazolyl, unsubstituted or lower alkyl-substituted 4,5-dihydro-2-oxazolyl or hydroxycarbamoyl; and $R_2$ is hydrogen, lower alkyl, phenyl-lower alkyl, carboxy-lower alkyl, lower alkoxycarbonyl-lower alkyl, halogen, hydroxy, lower alkoxy, lower alkanoyloxy, mercapto, lower alkylthio, phenyl-lower alkylthio, phenylthio, lower alkanoylthio, carboxy, lower alkoxycarbonyl or lower alkanoyl; the 7,8-dihydro derivatives thereof; and the compounds of Formula I*

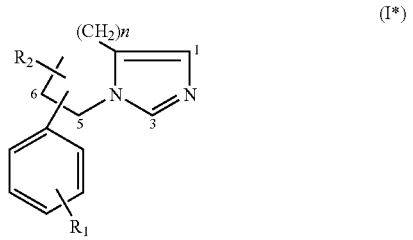

(I*)

wherein n is 0, 1, 2, 3 or 4; and $R_1$ and $R_2$ are as defined above for Formula I; it being possible for the phenyl ring in the radicals phenylsulfonyloxy, phenyliminomethyl, benzoyl, phenyl-lower alkyl, phenyl-lower alkylthio and phenylthio to be unsubstituted or substituted by lower alkyl, lower alkoxy or by halogen; it being possible in a compound of Formula I* for the two substituents $C_6H_4$—$R_1$ and $R_2$ to be linked to each of the saturated carbon atoms of the saturated ring, either both to the same carbon atom or both to different carbon atoms, and pharmaceutically acceptable salts thereof.

Individual compounds that may be given special mention here are:

(1) 5-(p-cyanophenyl)imidazo[1,5-a]pyridine,
(2) 5-(p-ethoxycarbonylphenyl)imidazo[1,5-a]pyridine,
(3) 5-(p-carboxyphenyl)imidazo[1,5-a]pyridine,
(4) 5-(p-tert-butylaminocarbonylphenyl)imidazo[1,5-a]pyridine,
(5) 5-(p-ethoxycarbonylphenyl)-5,6,7,8-tetrahydroimidazo[1,5-a]pyridine,
(6) 5-(p-carboxyphenyl)-5,6,7,8-tetrahydroimidazo[1,5-a]pyridine,
(7) 5-(p-carbamoylphenyl)-5,6,7,8-tetrahydroimidazo[1,5-a]pyridine,
(8) 5-(p-tolyl)-5,6,7,8-tetrahydroimidazo[1,5-a]pyridine,
(9) 5-(p-hydroxymethylphenyl)imidazo[1,5-a]pyridine,
(10) 5-(p-cyanophenyl)-7,8-dihydroimidazo[1,5-a]pyridine,
(11) 5-(p-bromophenyl)-5,6,7,8-tetrahydroimidazo[1,5-a]pyridine,
(12) 5-(p-hydroxymethylphenyl)-5,6,7,8-tetrahydroimidazo[1,5-a]pyridine,
(13) 5-(p-formylphenyl)-5,6,7,8-tetrahydroimidazo[1,5-a]pyridine,
(14) 5-(p-cyanophenyl)-5-methylthio-5,6,7,8-tetrahydroimidazo[1,5-a]pyridine,
(15) 5-(p-cyanophenyl)-5-ethoxycarbonyl-5,6,7,8-tetrahydroimidazo[1,5-a]pyridine,
(16) 5-(p-aminophenyl)-5,6,7,8-tetrahydroimidazo[1,5-a]pyridine,
(17) 5-(p-formylphenyl)imidazo[1,5-a]pyridine,
(18) 5-(p-carbamoylphenyl)imidazo[1,5-a]pyridine,
(19) 5H-5-(4-tert-butylaminocarbonylphenyl)-6,7-dihydropyrrolo[1,2-c]imidazole,
(20) 5H-5-(4-cyanophenyl)-6,7-dihydropyrrolo[1,2-c]imidazole,
(21) 5H-5-(4-cyanophenyl)-6,7,8,9-tetrahydroimidazo[1,5-a]azepine,
(22) 5-(4-cyanophenyl)-6-ethoxycarbonylmethyl-5,6,7,8-tetrahydroimidazo[1,5-a]pyridine,
(23) 5-(4-cyanophenyl)-6-carboxymethyl-5,6,7,8-tetrahydroimidazo[1,5-a]pyridine
(24) 5-benzyl-5-(4-cyanophenyl)-5,6,7,8-tetrahydroimidazo[1,5-a]pyridine,
(25) 7-(p-cyanophenyl)-5,6,7,8-tetrahydroimidazo[1,5-a]pyridine,
(26) 7-(p-carbamoylphenyl)-5,6,7,8-tetrahydroimidazo[1,5-a]pyridine,
(27) 5-(p-cyanophenyl)-5,6,7,8-tetrahydroimidazo[1,5-a]pyridine (=Fadrozol).

(b) The compounds of Formula I as defined in European Patent Publication No. EP-A 236 940. These are especially the compounds of Formula I

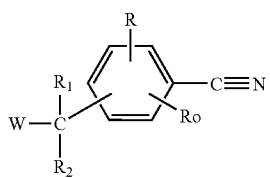

wherein R and $R_0$, independently of one another, are each hydrogen or lower alkyl, or R and $R_0$ at adjacent carbon atoms, together with the benzene ring to which they are bonded, form a naphthalene or tetrahydronaphthalene ring; wherein $R_1$ is hydrogen, lower alkyl, aryl, aryl-lower alkyl or lower alkenyl; $R_2$ is hydrogen, lower alkyl, aryl, aryl-lower alkyl, (lower alkyl, aryl or aryl-lower alkyl)-thio or lower alkenyl, or wherein $R_1$ and $R_2$ together are lower alkylidene or $C_4$-$C_6$ alkylene; wherein W is 1-imidazolyl, 1-(1,2,4 or 1,3,4)-triazolyl, 3-pyridyl or one of the mentioned heterocyclic radicals substituted by lower alkyl; and aryl within the context of the above definitions has the following meanings: phenyl that is unsubstituted or substituted by one or two substituents from the group lower alkyl, lower alkoxy, hydroxy, lower alkanoyloxy, nitro, amino, halogen, trifluoromethyl, cyano, carboxy, lower alkoxycarbonyl, carbamoyl, N-lower alkylcarbamoyl, N,N-di-lower alkylcarbamoyl, lower alkanoyl, benzoyl, lower alkylsulfonyl, sulfamoyl, N-lower alkylsulfamoyl and N,N-di-lower alkylsulfamoyl; also thienyl, indolyl, pyridyl or furyl, or one of the four last-mentioned heterocyclic radicals monosubstituted by lower alkyl, lower alkoxy, cyano or by halogen; and pharmaceutically acceptable salts thereof.

Individual compounds from that group that may be given special mention are:
(1) 4-[alpha-(4-cyanophenyl)-1-imidazolylmethyl]-benzonitrile,
(2) 4-[alpha-(3-pyridyl)-1-imidazolylmethyl]-benzonitrile,
(3) 4-[alpha-(4-cyanobenzyl)-1-imidazolylmethyl]-benzonitrile,
(4) 1-(4-cyanophenyl)-1-(1-imidazolyl)-ethylene,
(5) 4-[alpha-(4-cyanophenyl)-1-(1,2,4-triazolyl)methyl]-benzonitrile,
(6) 4-[alpha-(4-cyanophenyl)-3-pyridylmethyl]-benzonitrile.
(c) The compounds of Formula I as defined in European Patent Publication No. EP-A-408 509. These are especially the compounds of Formula I

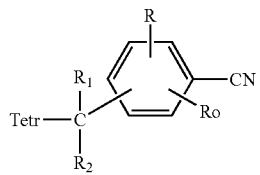

wherein Tetr is 1- or 2-tetrazolyl that is unsubstituted or substituted in the 5-position by lower alkyl, phenyl-lower alkyl or by lower alkanoyl; R and $R_2$, independently of one another, are each hydrogen; lower alkyl that is unsubstituted or substituted by hydroxy, lower alkoxy, halogen, carboxy, lower alkoxycarbonyl, (amino, lower alkylamino or di-lower alkylamino)-carbonyl or by cyano; lower alkenyl, aryl, heteroaryl, aryl-lower alkyl, $C_3$-$C_6$ cycloalkyl, $C_3$-$C_6$ cycloalkyl-lower alkyl, lower alkylthio, arylthio or aryl-lower alkylthio; or $R_1$ and $R_2$ together are straight-chained $C_4$-$C_6$ alkylene that is unsubstituted or substituted by lower alkyl, or are a group —$(CH_2)_m$-1,2-phenylene-$(CH_2)_n$— wherein m and n, independently of one another, are each 1 or 2 and 1,2-phenylene is unsubstituted or substituted in the same way as phenyl in the definition of aryl below, or are lower alkylidene that is unsubstituted or mono- or di-substituted by aryl; and R and $R_0$, independently of one another, are each hydrogen or lower alkyl; or R and $R_0$ together, located at adjacent carbon atoms of the benzene ring, are a benzo group that is unsubstituted or substituted in the same way as phenyl in the definition of aryl below; aryl in the above definitions being phenyl that is unsubstituted or substituted by one or more substituents from the group consisting of lower alkyl, lower alkoxy, hydroxy, lower alkanoyloxy, nitro, amino, halogen, trifluoromethyl, carboxy, lower alkoxycarbonyl, (amino, lower alkylamino or di-lower alkylamino)-carbonyl, cyano, lower alkanoyl, benzoyl, lower alkylsulfonyl and (amino, lower alkylamino or di-lower alkylamino)-sulfonyl; heteroaryl in the above definitions being an aromatic heterocyclic radical from the group consisting of pyrrolyl, pyrazolyl, imidazolyl, triazolyl, tetrazolyl, furanyl, thienyl, isoxazolyl, oxazolyl, oxadiazolyl, isothiazolyl, thiazolyl, thiadiazolyl, pyridyl, pyridazinyl, pyrimidyl, pyrazinyl, triazinyl, indolyl, isoindolyl, benzimidazolyl, benzotriazolyl, benzofuranyl, benzothienyl, benzoxazolyl, benzothiazolyl, benzoxadiazolyl, benzothiadiazolyl, quinolyl and isoquinolyl that is unsubstituted or substituted in the same way as phenyl in the definition of aryl above; and pharmaceutically acceptable salts thereof.

Individual compounds from that group that may be given special mention are:
(1) 4-(2-tetrazolyl)methyl-benzonitrile,
(2) 4-[a-(4-cyanophenyl)-(2-tetrazolyl)methyl]-benzonitrile,
(3) 1-cyano-4-(1-tetrazolyl)methyl-naphthalene,
(4) 4-[a-(4-cyanophenyl)-(1-tetrazolyl)methyl]-benzonitrile.
(d) The compounds of Formula I as defined in European Patent Application No. 91810110.6. These are especially the compounds of Formula I

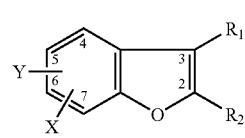

wherein X is halogen, cyano, carbamoyl, N-lower alkylcarbamoyl, N-cycloalkyl-lower alkylcarbamoyl, N,N-di-lower alkylcarbamoyl, N-arylcarbamoyl, hydroxy, lower alkoxy, aryl-lower alkoxy or aryloxy, wherein aryl is phenyl or naphthyl, each of which is unsubstituted or substituted by lower alkyl, hydroxy, lower alkoxy, halogen and/or by trifluoromethyl; Y is a group —$CH_2$—A wherein A is 1-imidazolyl, 1-(1,2,4-triazolyl), 1-(1,3,4-triazolyl), 1-(1,2,3-triazolyl), 1-(1,2,5-triazolyl), 1-tetrazolyl or 2-tetrazolyl, or Y is hydrogen, $R_1$ and $R_1$, independently of one another, are each hydrogen, lower alkyl or a group —$CH_2$—A as defined for Y, or $R_1$ and $R_2$ together are —$(CH_2)_n$— wherein n is 3, 4 or 5, with the proviso that one of the radicals Y, $R_1$ and $R_2$ is a group —$CH_2$—A, with the further proviso that in a group —$CH_2$—A as a meaning of $R_1$ or $R_2$, A is other than 1-imidazolyl when X is bromine, cyano or carbamoyl, and with the proviso that in a group —$CH_2$—A as a meaning of Y, A is other than 1-imidazolyl when X is halogen or lower alkoxy, $R_1$ is hydrogen and $R_2$ is hydrogen or lower alkyl, and pharmaceutically acceptable salts thereof.

Individual compounds from that group that may be given special mention are:
(1) 7-cyano-4-[1-(1,2,4-triazolyl)methyl]-2,3-dimethylbenzofuran,
(2) 7-cyano-4-(1-imidazolylmethyl)-2,3-dimethylbenzofuran,
(3) 7-carbamoyl-4-(1-imidazolylmethyl)-2,3-dimethylbenzofuran,
(4) 7-N-(cyclohexylmethyl)carbamoyl-4-(1-imidazolylmethyl)-2,3-dimethylbenzofuran.

(e) The compounds of Formula I as defined in Swiss Patent Application No. 1339/90-7. These are especially the compounds of Formula I

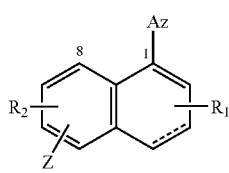

(I)

wherein the dotted line denotes an additional bond or no additional bond, Az is imidazolyl, triazolyl or tetrazolyl bonded via a ring nitrogen atom, each of those radicals being unsubstituted or substituted at carbon atoms by lower alkyl or by aryl-lower alkyl, Z is carboxy, lower alkoxycarbonyl, carbamoyl, N-lower alkylcarbamoyl, N,N-di-lower alkylcarbamoyl, N-arylcarbamoyl, cyano, halogen, hydroxy, lower alkoxy, aryl-lower alkoxy, aryloxy, lower alkyl, trifluoromethyl or aryl-lower alkyl, and $R_1$ and $R_2$, independently of one another, are each hydrogen, lower alkyl, lower alkoxy, hydroxy, halogen or trifluoromethyl; aryl being phenyl or naphthyl each of which is unsubstituted or substituted by one or two substituents from the group consisting of lower alkyl, lower alkoxy, hydroxy, halogen and trifluoromethyl; with the proviso that neither Z nor $R_2$ is hydroxy in the 8-position, and pharmaceutically acceptable salts thereof.

Individual compounds from that group that may be given special mention are:
(1) 6-cyano-1-(1-imidazolyl)-3,4-dihydronaphthalene,
(2) 6-cyano-1-[1-(1,2,4-triazolyl)]-3,4-dihydronaphthalene,
(3) 6-chloro-1-(1-imidazolyl)-3,4-dihydronaphthalene,
(4) 6-bromo-1-(1-imidazolyl)-3,4-dihydronaphthalene.

(f) The compounds of Formula I as defined in Swiss Patent Application No. 3014/90-0. These are especially the compounds of Formula I

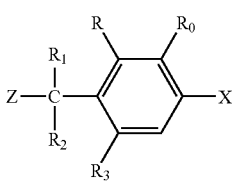

(I)

wherein Z is a five-membered nitrogen-containing heteroaromatic ting selected from the group 5-isothiazolyl, 5-thiazolyl, 5-isoxazolyl, 5-oxazolyl, 5-(1,2,3-thiadiazolyl), 5-(1,2,3-oxadiazolyl), 3-(1,2,5-thiadiazolyl), 3-(1,2,5-oxadiazolyl), 4-isothiazolyl, 4-isoxazolyl, 4-(1,2,3-thiadiazolyl), 4-(1,2,3-oxadiazolyl), 2-(1,3,4-thiadiazolyl), 2-(1,3,4-oxadiazolyl), 5-(1,2,4-thiadiazolyl) and 5-(1,2,4-oxadiazolyl); R and $R_0$ are hydrogen; or R and $R_0$ together are a benzo group that is unsubstituted or substituted by lower alkyl, lower alkoxy, hydroxy, halogen or by trifluoromethyl; $R_1$ is hydrogen, hydroxy, chlorine or fluorine; $R_3$ is hydrogen; $R_2$ is hydrogen, lower alkyl or phenyl that is unsubstituted or substituted by lower alkyl, lower alkoxy, hydroxy, halogen, trifluoromethyl or by cyano; or $R_1$ and $R_2$ together are methylidene; or $R_2$ and $R_3$ together are —$(CH_2)_3$—; or $R_1$ and $R_2$ and $R_3$ together are a group =CH—$(CH_2)_2$—wherein the single bone is linked to the benzene ring; X is cyano; and X may also be halogen when $R_2$ and $R_3$ together are —$(CH_2)_3$— or $R_1$ and $R_1$ and $R_3$ together are a group =CH—$(CH_2)_2$—; and pharmaceutically acceptable salts thereof.

Individual compounds from that group that may be given special mention are:
(1) 4-[a-(4-cyanophenyl)-a-hydroxy-5-isothiazolylmethyl]-benzonitrile.
(2) 4-[a-(4-cyanophenyl)-5-isothiazolylmethyl]-benzonitrile,
(3) 4-[a-(4-cyanophenyl)-5-thiazolylmethyl]-benzonitrile,
(4) 1-(4-cyanophenyl)-1-(5-thiazolyl)-ethylene,
(5) 6-cyano-1-(5-isothiazolyl)-3,4-dihydronaphthalene,
(6) 6-cyano-1-(5-thiazolyl)-3,4-dihydronaphthalene.

(g) The compounds of formula VI as defined in Swiss Patent Application No. 3014/90-0.

These are especially the compounds of formula VI

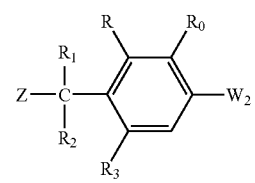

(VI)

wherein Z is a five-membered nitrogen-containing heteroaromatic ring selected from the group 5-isothiazolyl, 5-thiazolyl, 5-isoxazolyl, 5-oxazolyl, 5-(1,2,3-thiadiazolyl). 5-(1,2,3-oxadiazolyl) 3-(1,2,5-thiadiazolyl), 3-(1,2,5-oxadiazolyl), 4-isothiazolyl. 4-isoxazolyl, 4-(1,2,3-thiadiazolyl), 4-(1,2,3-oxadiazolyl), 2-(1,3,4-thiadiazolyl), 2-(1,3,4-oxadiazolyl), 5-(1,2,4-thiadiazolyl) and 5-(1,2,4-oxadiazolyl); R and $R_0$ are each hydrogen; or R and $R_0$ together are a benzo group that is unsubstituted or substituted by lower alkyl, lower alkoxy, hydroxy, halogen or by trifluoromethyl; $R_1$ is hydrogen, hydroxy, chlorine or fluorine; $R_3$ is hydrogen; $R_2$ is hydrogen, lower alkyl or phenyl that is unsubstituted or substituted by lower alkyl, lower alkoxy, hydroxy, halogen, trifluoromethyl, aryl-lower alkoxy or by aryloxy; or $R_1$ and $R_2$ together are methylidene, and $W_2$ is halogen, hydroxy, lower alkoxy, aryl-lower alkoxy or aryloxy; aryl in each case being phenyl that is unsubstituted or substituted by lower alkyl, lower alkoxy, hydroxy, halogen or by trifluoromethyl; and pharmaceutically acceptable salts thereof.

Individual compounds from that group that may be given special mention are:
(1) bis(4,4'-bromophenyl)-(5-isothiazolyl)methanol,
(2) bis(4,4'-bromophenyl)-(5-isothiazolyl)methane,
(3) bis(4,4'-bromophenyl)-(5-thiazolyl)methanol,
(4) bis(4,4'-bromophenyl)-(5-thiazolyl)methane, (h) The compounds of Formula I as defined in Swiss Patent Application No. 3923/90-4. These are especially the compounds of Formula I

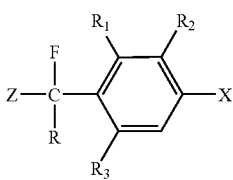
(I)

wherein Z is imidazolyl, triazolyl, tetrazolyl, pyrrolyl, pyrazolyl, indolyl, isoindolyl, benzimidazolyl, benzopyrazolyl, benzotriazolyl, pyridyl, pyrimidyl, pyrazinyl, pyridazinyl, triazinyl, quinolinyl or isoquinolinyl, all those radicals being bonded via their heterocyclic rings and all those radicals being unsubstituted or substituted by lower alkyl, hydroxy, lower alkoxy, halogen or by trifluoromethyl: $R_1$ and $R_2$, independently of one another, are each hydrogen or lower alkyl; or $R_1$ and $R_2$ together are $C_3$-$C_4$ alkylene, or a benzo group that is unsubstituted or substituted as indicated below for aryl; R is hydrogen, lower alkyl, aryl or heteroaryl, and X is cyano, carbamoyl, N-lower alkylcarbamoyl, N,N-di-lower alkylcarbamoyl, N,N-lower alkylenecarbamoyl; N,N-lower alkylenecarbamoyl interrupted by —O—, —S— or —NR"—, wherein R" is hydrogen, lower alkyl or lower alkanoyl; N-cycloalkylcarbamoyl, N-(lower alkyl-substituted cycloalkyl)-carbamoyl, N-cycloalkyl-lower alkylcarbamoyl, N-(lower alkyl-substituted cycloalkyl)-lower alkylcarbamoyl, N-aryl-lower alkylcarbamoyl, N-arylcarbamoyl, -hydroxycarbamoyl, hydroxy, lower alkoxy, aryl-lower alkoxy or aryloxy; and wherein X is also halogen when Z is imidazolyl, triazolyl, tetrazolyl, pyrrolyl, pyrazolyl, indolyl, isoindolyl, benzimidazolyl, benzopyrazolyl or benzotriazolyl; wherein aryl is phenyl or naphthyl, these radicals being unsubstituted or substituted by from 1 to 4 substituents from the group consisting of lower alkyl, lower alkenyl, lower alkynyl, lower alkylene (linked to two adjacent carbon atoms), $C_3$-$C_8$ cycloalkyl, phenyl-lower alkyl, phenyl; lower alkyl that is substituted in turn by hydroxy, lower alkoxy, phenyl-lower alkoxy, lower alkanoyloxy, halogen, amino, lower alkylamino, di-lower alkylamino, mercapto, lower alkylthio, lower alkylsulfinyl, lower alkylsulfonyl, carboxy, lower alkoxycarbonyl, carbamoyl, N-lower alkylcarbamoyl, N,N-di-lower alkylcarbamoyl and/or by cyano; hydroxy; lower alkoxy, halo-lower alkoxy, phenyl-lower alkoxy, phenoxy, lower alkenyloxy, halo-lower alkenyloxy, lower alkynyloxy, lower alkylenedioxy (linked to two adjacent carbon atoms), lower alkanoyloxy, phenyl-lower alkanoyloxy, phenylcarbonyloxy, mercapto, lower alkylthio, phenyl-lower alkylthio, phenylthio, lower alkylsulfinyl, phenyl-lower alkylsulfinyl, phenylsulfinyl, lower alkylsulfonyl, phenyl-lower alkylsulfonyl, phenylsulfonyl, halogen, nitro, amino, lower alkylamino, $C_3$-$C_8$ cycloalkylamino, phenyl-lower alkylamino, phenylamino, di-lower alkylamino, N-lower alkyl-N-phenylamino, N-lower alkyl-N-phenyl-lower alkylamino; lower alkyleneamino or lower alkyleneamino interrupted by —O—, —S— or —NR"— (wherein R" is hydrogen, lower alkyl or lower alkanoyl); lower alkanoylamino, phenyl-lower alkanoylamino, phenylcarbonylamino, lower alkanoyl, phenyl-lower alkanoyl, phenylcarbonyl, carboxy, lower alkoxycarbonyl, carbamoyl, N-lower alkylcarbamoyl, N,N-di-lower alkylcarbamoyl, N,N-lower alkylenecarbamoyl; N,N-lower alkylenecarbamoyl interrupted by —O—, —S— or —NR"—, wherein R" is hydrogen, lower alkyl or lower alkanoyl; N-cycloalkylcarbamoyl, N-(lower alkyl-substituted cycloalkyl)-carbamoyl, -cycloalkyl-lower alkylcarbamoyl, N-(lower alkyl-substituted cycloalkyl)-lower alkylcarbamoyl, N-hydroxycarbamoyl, N-phenyl-lower alkylcarbamoyl, -phenylcarbamoyl, cyano, sulfo, lower alkoxysulfonyl, sulfamoyl, N-lower alkylsulfamoyl, N,N-di-lower alkylsulfamoyl and N-phenylsulfamoyl; the phenyl groups occurring in the substituents of phenyl and naphthyl in turn being unsubstituted or substituted by lower alkyl, lower alkoxy, hydroxy, halogen and/or by trifluoromethyl; wherein heteroaryl is indolyl, isoindolyl, benzimidazolyl, benzopyrazolyl, benzotriazolyl, benzo[b]furanyl, benzo[b]thienyl, benzoxazolyl or benzothiazolyl, those radicals being unsubstituted or substituted by from 1 to 3 identical or different substituents selected from lower alkyl, hydroxy, lower alkoxy, halogen, cyano and trifluoromethyl; and pharmaceutically acceptable salts thereof.

Those compounds are especially the compounds of Formula I whereto Z is 1-imidazolyl, 1-(1,2,4-triazolyl), 1-(1,3,4-triazolyl), 1-(1,2,3-triazolyl), 1-tetrazolyl, 2-tetrazolyl, 3-pyridyl, 4-pyridyl, 4-pyrimidyl, 5-pyrimidinyl or 2-pyrazinyl; $R_1$ and $R_2$, independently of one another, are each hydrogen or lower alkyl; or $R_1$ and $R_2$ together are 1,4-butylene or a benzo group; R is lower alkyl; phenyl that is unsubstituted or substituted by cyano, carbamoyl, halogen, lower alkyl, trifluoromethyl, hydroxy, lower alkoxy or by phenoxy; or benzotriazolyl or benzo[b]furanyl, the last two radicals being unsubstituted or substituted by from 1 to 3-identical or different substituents selected from lower alkyl, halogen and cyano; and X is cyano or carbamoyl; and wherein X is also halogen when Z is 1-imidazolyl, 1-(1,2,4-triazolyl), 1-(1,3,4-triazolyl), 1-(1,2,3-triazolyl), 1-tetrazolyl 2-tetrazolyl; and pharmaceutically acceptable salts thereof.

Individual compounds that may be given special mention here are:
(1) 4-[a-4-cyanophenyl)-a-fluoro-1-(1,2,4-triazolyl)methyl]-benzonitrile,
(2) 4-[a-(4-cyanophenyl)-a-fluoro-(2-tetrazolyl)methyl]-benzonitrile,
(3) 4-[a-(4-cyanophenyl)-a-fluoro-(1-tetrazolyl)methyl]-benzonitrile,
(4) 4-[a-(4-cyanophenyl)-a-fluoro-(1-imidazolyl)methyl]-benzonitrile,
(5) 1-methyl-6-[a-(4-chlorophenyl)-a-fluoro-1-(1,2,4-triazolyl)methyl]-benzotriazole,
(6) 4-[a-(4-cyanophenyl)-a-fluoro-1-(1,2,3-triazolyl)methyl]-benzo nitrile,
(7) 7-cyano-4-[a-(4-cyanophenyl)-a-fluoro-1-(1,2,4-triazolyl)methyl]-2,3-dimethylbenzo[b]furan,
(8) 4-[a-(4-bromophenyl)-a-fluoro-1-(1,2,4-triazolyl)methyl]-benzonitrile,
(9) 4-[a-(4-cyanophenyl)-a-fluoro-(5-pyrimidyl)methyl]-benzonitrile,
(10) 4-[a-(4-bromophenyl)-a-fluoro-(5-pyrimidyl)methyl]-benzonitrile,
(11) 4-[a-(4-cyanophenyl)-a-fluoro-(3-pyridyl)methyl]-benzonitrile,
(12) 7-bromo-4-[a-(4-cyanophenyl)-a-fluoro-(1-imidazolyl)methyl]-2,3-dimethylbenzo[b]furan,
(13) 7-bromo-4-[a-(4-cyanophenyl)-a-fluoro-1-(1,2,4-triazolyl)methyl]-2,3-dimethylbenzo[b]furan,
(14) 4-[a-(4-cyanophenyl)-a-fluoro-(5-pyrimidyl)methyl]-benzonitrile,
(15) 4-[a-(4-bromophenyl)-a-fluoro-(5-pyrimidyl)methyl]-benzonitrile,
(16) 4-[a-(4-cyanophenyl)-1-(1,2,3-triazolyl)methyl]-benzonitrile,
(17) 2,3-dimethyl-4-[a-(4-cyanophenyl)-1-(1,2,4-triazolyl)methyl]-7-cyano-benzo[b]furan,
(18) 4-[a-(4-cyanophenyl)-(5-pyrimidyl)methyl]-benzonitrile,

(19) 4-[a-(4-bromophenyl)-(5-pyrimidyl)methyl]-benzonitrile,
(20) 2,3-dimethyl-4-[a-(4-cyanophenyl)-(1-imidazolyl)methyl]-7-bromo-benzo[b]furan,
(21) 2,3-dimethyl-4-[a-(4-cyanophenyl)-1-(1,2,4-triazolyl)methyl]-7-bromo-benzo-[b]furan.

(i) The compounds of Formula I as defined in European Patent Publication No. EP-A-114 033. These are especially the compounds of Formula I

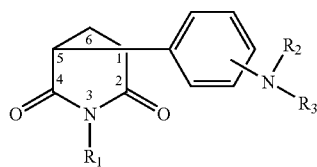

wherein $R_1$ is hydrogen, $R_2$ is hydrogen, sulfo, $C_1$-$C_7$ alkanoyl or $C_1$-$C_7$ alkanesulfonyl and $R_3$ is hydrogen, or wherein $R_1$ is $C_1$-$C_{12}$ alkyl, $C_2$-$C_{12}$ alkenyl, $C_2$-$C_7$ alkynyl, $C_3$-$C_{10}$ cycloalkyl, $C_3$-$C_{10}$ cycloalkenyl, $C_3$-$C_6$ cycloalkyl-$C_1$-$C_4$ alkyl, $C_3$-$C_6$ cycloalkyl-$C_2$-$C_4$ alkenyl or $C_3$-$C_6$ cycloalkenyl-$C_1$-$C_4$ alkyl, $R_2$ is hydrogen, $C_1$-$C_7$ alkyl, sulfo, $C_1$-$C_7$ alkanoyl or $C_1$-$C_7$ alkanesulfonyl and $R_3$ is hydrogen or $C_1$-$C_7$ alkyl, and salts of those compounds.

Individual compounds from that group that may be given special mention are:
(1) 1-(4-aminophenyl)-3-methyl-3-azabicyclo[3.1.0]hexane-2,4-dione,
(2) 1-(4-aminophenyl)-3-n-propyl-3-azabicyclo[3.1.0]hexane-2,4-dione,
(3) 1-(4-aminophenyl)-3-isobutyl-3-azabicyclo[3.1.0]hexane-2,4-dione,
(4) 1-(4-aminophenyl)-3-n-heptyl-3-azabicyclo[3.1.0]hexane-2,4-dione,
(5) 1-(4-aminophenyl)-3-cyclohexylmethyl-3-azabicyclo[3.1.0]hexane-2,4-dione.

(j) The compounds of Formula I as defined in European Patent Publication No. EP-A-166 692. These are especially the compounds of Formula I

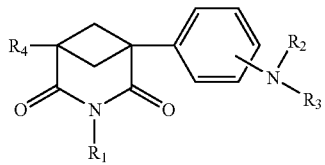

wherein $R_1$ is hydrogen, alkyl having from 1 to 12 carbon atoms, alkenyl having from 2 to 12 carbon atoms, lower alkynyl, cycloalkyl or cycloalkenyl each having from 3 to 10 carbon atoms, cycloalkyl-lower alkyl having from 4 to 10 carbon atoms, cycloalkyl-lower alkenyl having from 5 to 10 carbon atoms, cycloalkenyl-lower alkyl having from 4 to 10 carbon atoms, or aryl having from 6 to 12 carbon atoms or aryl-lower alkyl having from 7 to 15 carbon atoms, each of which is unsubstituted or substituted by lower alkyl, hydroxy, lower alkoxy, acyloxy, amino, lower alkylamino, di-lower alkylamino, acylamino amino or by halogen, $R_2$ is hydrogen, lower alkyl, sulfo, lower alkanoyl or lower alkanesulfonyl, sulfonyl, $R_3$ is hydrogen or lower alkyl and $R_4$ is hydrogen, lower alkyl, phenyl or phenyl substituted by —N($R_2$)($R_3$), and salts thereof, radicals described as "lower" containing up to and including 7 carbon atoms.

Individual compounds from that group that may be given special mention are:
(1) 1-(4-aminophenyl)-3-n-propyl-3-azabicyclo[3.1.1]heptane-2,4-dione,
(2) 1-(4-aminophenyl)-3-methyl-3-azabicyclo[3.1.1]heptane-2,4-dione,
(3) 1-(4-aminophenyl)-3-n-decyl-3-azabicyclo[3.1.1]heptane-2,4-dione,
(4) 1-(4-aminophenyl)-3-cyclohexyl-3-azabicyclo[3.1.1]heptane-2,4-dione,
(5) 1-(4-aminophenyl)-3-cyclohexylmethyl-3-azabicyclo[3.1.1]heptane-2,4-dione.

(k) The compounds of Formula I as defined in European Patent Publication No. EP-A-356 673. These are especially the compounds of Formula I

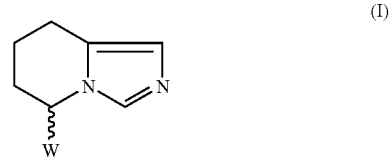

wherein W (a) is a 2-naphthyl or 1-anthryl radical, wherein each benzene ring is unsubstituted or substituted by a substituent selected from halogen, hydroxy, carboxy, cyano and nitro; or (.beta.) is 4-pyridyl, 2-pyrimidyl or 2-pyrazinyl, each of those radicals being unsubstituted or substituted by a substituent selected from halogen, cyano, nitro, $C_1$-$C_4$ alkoxy and $C_2$-$C_5$ alkoxycarbonyl; and pharmaceutically acceptable salts thereof.

Individual compounds from that group that may be given special mention are:
(1) 5-(2'-naphthyl)-5,6,7,8-tetrahydroimidazo[1,5-a]pyridine,
(2) 5-(4'-pyridyl)-5,6,7,8-tetrahydroimidazo[1,5-a]pyridine.

(l) The compounds of Formula I or Ia as defined in European Patent Publication No. EP-A-337 929. These are especially the compounds of Formula I/Ia

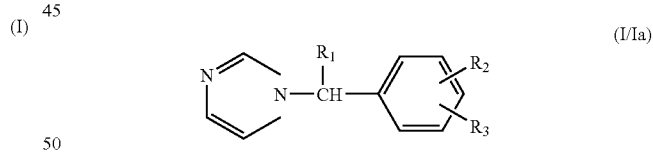

wherein $R_1$ is hydrogen, methyl, ethyl, propyl, propenyl, isopropyl, butyl, hexyl, octyl, decyl, cyclopentyl, cyclohexyl, cyclopentylmethyl, cyclohexylmethyl or benzyl, $R_2$ is benzyloxy, 3-bromo-, 4-bromo-, 4-chloro-, 2,3-, 2,4-, 4,5- or 4,6-dichloro-benzyloxy, and $R_3$ is cyano; $C_2$-$C_{10}$ alkanoyl that is unsubstituted or mono- or poly-substituted by halogen, methoxy, amino, hydroxy and/or by cyano; benzoyl that is unsubstituted or substituted by one or more substituents from the group halogen, $C_1$-$C_4$ alkyl, methoxy, amino, hydroxy and cyano; carboxy, (methoxy, ethoxy or butoxy)-carbonyl, carbamoyl, N-isopropylcarbamoyl, N-phenylcarbamoyl, N-pyrrolidylcarbonyl, nitro or amino; and salts thereof.

Individual compounds from that group that may be given special mention are:
(1) 4-(2,4-dichlorobenzyloxy)-3-[1-(1-imidazolyl)-butyl]-benzonitrile, (2) (4-(4-bromobenzyloxy)-3-[1-(1-imidazolyl)-butyl]-phenyl pentyl ketone,
(3) 4-(4-bromobenzyloxy)-3-[1-(1-imidazolyl)-butyl]-benzanilide,
(4) 4-(4-bromobenzyloxy)-3-[1-(1-imidazolyl)-butyl]-benzoic acid,
(5) 3-(2,4-dichlorobenzyloxy)-4-[1-(1-imidazolyl)-butyl]-benzonitrile,
(6) 3-(2,4-dichlorobenzyloxy)-4-[1-(1-imidazolyl)-butyl]-benzoic acid methyl ester,
(7) 3-(2,4-dichlorobenzyloxy)-4-[1-(1-imidazolyl)-butyl]-benzoic acid,
(8) 3-(3-bromobenzyloxy)-4-[1-(1-imidazolyl)-butyl]-benzonitrile,
(9) 4-(3-bromobenzyloxy)-3-[1-(1-imidazolyl)-butyl]-benzonitrile,
(10) 3-(4-bromobenzyloxy)-4-[1-(1-imidazolyl)-butyl]-benzoic acid,
(11) 3-(4-bromobenzyloxy)-4-[1-(1-imidazolyl)-butyl]-benzanilide,
(12) 3-(4-bromobenzyloxy)-4-[1-(1-imidazolyl)-butyl]-phenyl pentyl ketone,
(13) 4-(4-bromobenzyloxy)-3-[1-(1-imidazolyl)-butyl]-benzonitrile,
(14) 3-(4-bromobenzyloxy)-4-[1-(1-imidazolyl)-butyl]-benzonitrile,
(15) 4-nitro-2-[1-(1-imidazolyl)-butyl]-phenyl-(2,4-dichlorobenzyl)ether,
(16) 4-amino-2-[1-(1-imidazolyl)-butyl]-phenyl-(2,4-dichlorobenzyl)ether,
(17) (2,4-dichlorobenzyl)-[2-(1-imidazolyl-methyl)-4-nitrophenyl]ether.
(m) The compounds of Formula I as defined in European Patent Publication No. EP-A-337 928. These are especially the compounds of Formula I

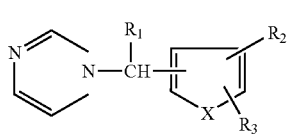

(I)

wherein $R_1$ is hydrogen, methyl, ethyl, propyl, propenyl, isopropyl, butyl, hexyl, octyl, decyl, cyclopentyl, cyclohexyl, cyclopentylmethyl, cyclohexylmethyl or benzyl, $R_2$ is hydrogen, halogen, cyano, methyl, hydroxymethyl, cyanomethyl, methoxymethyl, pyrrolidinylmethyl, carboxy, (methoxy, ethoxy or butoxy)-carbonyl, carbamoyl, -isopropylcarbamoyl, N-phenylcarbamoyl, N-pyrrolidylcarbonyl; $C_2$-$C_{10}$ alkanoyl that is unsubstituted or mono- or poly-substituted by halogen, methoxy, ethoxy, amino, hydroxy and/or by cyano; or benzoyl that is unsubstituted or substituted by one or more substituents from the group halogen, $C_1$-$C_4$ alkyl, methoxy, ethoxy, amino, hydroxy and cyano, $R_3$ is hydrogen, benzyloxy, 3-bromo-, 4-bromo-, 4-chloro-, 2,3-, 2,4-, 4,5- or 4,6-dichlorobenzyloxy, and X is —CH═—; —CH═N(—O)— or —S—; and salts thereof.

Individual compounds from that group that may be given special mention are:
(1) 5-[1-(1-imidazolyl)-butyl]-thiophene-2-carbonitrile,
(2) 2-[1-(1-imidazolyl)-butyl]-thiophene-4-carbonitrile,
(3) 2-[1-(1-imidazolyl)-butyl]-4-bromo-thiophene,
(4) 2-[1-(1-imidazolyl)-butyl]-5-bromo-thiophene,
(5) 5-[1-(1-imidazolyl)-butyl]-2-thienyl pentyl ketone,
(6) 5-[1-(1-imidazolyl)-butyl]-2-thienyl ethyl ketone,
(7) 5-(4-chlorobenzyloxy)-4-[1-(1-imidazolyl)-pentyl]-pyridine-2-carbonitrile,
(8) 3-(4-chlorobenzyloxy)-4-[1-(1-imidazolyl)-pentyl]-pyridine-2-carbonitrile,
(9) 3-(4-chlorobenzyloxy)-4-[1-(1-imidazolyl)-pentyl]-pyridine-N-oxide,
(10) 3-(4-chlorobenzyloxy)-4-[1-(1-imidazolyl)-pentyl]-pyridine.
(n) The compounds of Formula I as defined in European Patent Publication No. EP-A-340 153. These are especially the compounds of Formula I

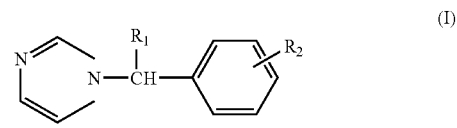

(I)

wherein $R_1$ is hydrogen, methyl, ethyl, propyl, propenyl, isopropyl, butyl, hexyl, octyl, decyl, cyclopentyl, cyclohexyl, cyclopentylmethyl, cyclohexylmethyl or benzyl, and $R_2$ is a radical from the group methyl, ethyl, propyl, benzyl, phenyl and ethenyl that is substituted by hydroxy, cyano, methoxy, butoxy, phenoxy, amino, pyrrolidinyl, carboxy, lower alkoxycarbonyl or by carbamoyl; or $R_2$ is formyl or derivatised formyl that can be obtained by reaction of the formyl group with an amine or amine derivative from the group hydroxylamine, O-methylhydroxylamine, O-ethylhydroxylamine, O-allylhydroxylamine, O-benzylhydroxylamine, O-4-nitrobenzyloxyhydroxylamine, O-2,3,4,5,6-pentafluorobenzyloxyhydroxylamine, semicarbazide, thiosemicarbazide, ethylamine and aniline; acetyl, propionyl, butyryl, valeryl, caproyl; benzoyl that is unsubstituted or substituted by one or more substituents from the group halogen, $C_1$-$C_4$-alkyl, methoxy, amino, hydroxy and cyano; carboxy, (methoxy, ethoxy or butoxy)carbonyl, carbamoyl, N-isopropylcarbamoyl, N-phenylcarbamoyl or N-pyrrolidylcarbonyl; and salts thereof.

Individual compounds from that group that may be given special mention are:
(1) 4-(1-(1-imidazolyl)-butyl)-benzoic acid methyl ester,
(2) 4-(1-(1-imidazolyl)-butyl)-benzoic acid butyl ester,
(3) 4-(1-(1-imidazolyl)-butyl)-phenyl-acetonitrile,
(4) 4-(1-(1-imidazolyl)-butyl)-benzaldehyde,
(5) 4-(1-(1-imidazolyl)-butyl)-benzyl alcohol,
(6) {4-[1-(1-imidazolyl)-butyl]-phenyl}-2-propyl ketone,
(7) 4-[1-(1-imidazolyl)-butyl]-phenyl propyl ketone,
(8) 4-[1-(1-imidazolyl)-butyl]-phenyl butyl ketone,
(9) 4-[1-(1-imidazolyl)-butyl]-phenyl pentyl ketone,
(10) 4-[1-(1-imidazolyl)-butyl]-phenyl hexyl ketone.
(o) The compounds of Formula I as defined in German Patent Application No. DE-A-4 014 006. These are especially the compounds of Formula I

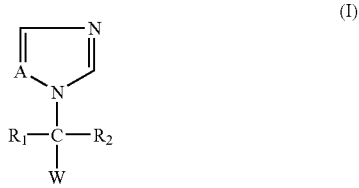

(I)

wherein A is an N-atom or a CH radical and W is a radical of the formula

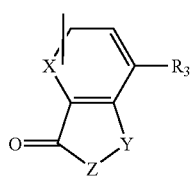

wherein X is an oxygen or a sulfur atom or a —CH=CH— group and Y is a methylene group, an oxygen or a sulfur atom and Z is a —(CH$_2$)$_n$— group wherein n=1, 2 or 3 and either a) R$_3$ in W is a hydrogen atom and R$_1$ and R$_2$, independently of one another, are each a hydrogen atom, a C$_1$- to C$_{10}$ alkyl group or a C$_3$- to C$_7$ cycloalkyl group, or b) R$_2$ is as defined under a) and R$_1$ together with R$_3$ forms a —(CH$_2$)$_m$— group wherein m=2, 3, or 4, and their pharmaceutically acceptable addition salts with acids.

Individual compounds from that group that may be given special mention are:

(1) 5-[1-(1-imidazolyl)-butyl]-1-indanone,
(2) 7-[1-(1-imidazolyl)-butyl]-1-indanone,
(3) 6-[1-(1-imidazolyl)-butyl]-1-indanone,
(4) 6-(1-imidazolyl)-6,7,8,9-tetrahydro-1H-benz[e]inden-3 (2H)-one,
(5) 2-[1-(1-imidazolyl)-butyl]-4,5-dihydro-6-oxo-cyclopenta[b]-thiophene,
(6) 6-[1-(1-imidazolyl)-butyl]-3,4-dihydro-2H-naphthalen-1-one,
(7) 2-[1-(1-imidazolyl)-butyl]-6,7-dihydro-5H-benzo[b]thiophen-4-one,
(8) 6-[1-(1-imidazolyl)-butyl]-2H-benzo[b]furan-3-one,
(9) 5-[cyclohexyl-(1-imidazolyl)-methyl]-1-indanone,
(10) 2-[1-(1-imidazolyl)-butyl]-4,5-dihydro-6H-benzo[b]thiophen-7-one,
(11) 5-[1-(1-imidazolyl)-1-propyl-butyl]-1-indanone,
(12) 2-[1-(1-imidazolyl)-butyl]-4,5-dihydro-6H-benzo[b]thiophen-7-one,
(13) 2-[1-(1-imidazolyl)-butyl]-4,5-dihydro-6-oxo-cyclopenta[b]-thiophene,
(14) 5-(1-imidazolylmethyl)-1-indanone,
(15) 5-[1-(1,2,4-triazolyl)-methyl]-1-indanone.

(p) The compounds of Formula I as disclosed in German Patent Application No. DE-A-3 926 365. These are especially the compounds of Formula I

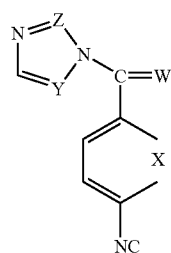

wherein W' is a cyclopentylidene, cyclohexylidene, cycloheptylidene or 2-adamantylidene radical, X is the grouping —CH=CH—, an oxygen or a sulfur atom, and Y and Z, independently of one another, are each a methine group (CH) or a nitrogen atom, and their pharmaceutically acceptable addition salts with acids.

Individual compounds from that group that may be given special mention are:

(1) 4-[1-cyclohexylidene-1-(imidazolyl)-methyl]-benzonitrile,
(2) 4-[1-cyclopentylidene-1-(imidazolyl)-methyl]-benzonitrile,
(3) 4-[1-cycloheptylidene-1-(imidazolyl)-methyl]-benzonitrile,
(4) 4-[2-adamantylidene-1-(imidazolyl)-methyl]-benzonitrile,
(5) 4-[1-cyclohexylidene-1-(1,2,4-triazolyl)-methyl]-benzonitrile,
(6) 4-[1-cyclopentylidene-1-(1,2,4-triazolyl)-methyl]-benzonitrile,
(7) 4-[1-cycloheptylidene-1-(1,2,4-triazolyl)-methyl]-benzonitrile,
(8) 4-[2-adamantylidene-1-(1,2,4-triazolyl)-methyl]-benzonitrile,
(9) 4-[1-cyclohexylidene-1-(1,2,3-triazolyl)-methyl]-benzonitrile,
(10) 4-[1-cyclopentylidene-1-(1,2,3-triazolyl)-methyl]-benzonitrile,
(11) 5-[cyclohexylidene-1-imidazolylmethyl]-thiophene-2-carbonitrile.

(q) The compounds of Formula I as defined in German Patent Application No. DE-A-3 740 125. These are especially the compounds of Formula I

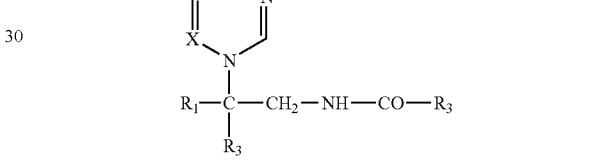

wherein X is CH or N, R$_1$ and R$_2$ are identical or different and are each phenyl or halophenyl, and R$_3$ is C$_1$-C$_4$ alkyl; C$_1$-C$_4$ alkyl substituted by CN, C$_1$-C$_4$ alkoxy, benzyloxy or by C$_1$-C$_4$ alkoxy-(mono-, di- or tri-)ethyleneoxy; C$_1$-C$_4$ alkoxy, phenyl; phenyl that is substituted by halogen or by cyano; a C$_5$-C$_7$ cycloalkyl group that is optionally condensed by benzene, or is thienyl, pyridyl or 2- or 3-indolyl; and acid addition salts thereof.

An individual compound from that group that may be given special mention is:

(1) 2,2-bis(4-chlorophenyl)-2-(1H-imidazol-1-yl)-1-(4-chlorobenzoyl-amino) ethane.

(r) The compounds of Formula I as defined in European Patent Publication No. EP-A-293 978. These are especially the compounds of Formula I

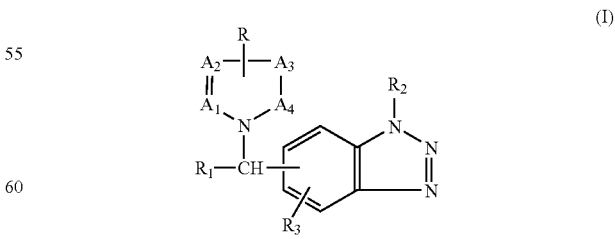

pharmaceutically acceptable salts and stereochemically isomeric forms thereof, wherein -A$_1$=A$_2$-A$_3$=A$_4$- is a divalent radical selected from —CH=N—CH=CH—, —CH=N—CH=N— and —CH=N—N=CH—, R is hydrogen or $C_1$-$C_6$ alkyl; $R_1$ is hydrogen, $C_1$-$C_{10}$ alkyl, $C_3$-$C_7$ cycloalkyl, $Ar_1$, $Ar_2$—$C_1'$-$C_6$ alkyl, $C_2$-$C_6$ alkenyl or $C_2$-$C_6$ alkynyl: $R_2$ is hydrogen; $C_1$-$C_{10}$ alkyl that is unsubstituted or substituted by $Ar_1$; $C_3$-$C_7$ cycloalkyl, hydroxy, $C_1$-$C_6$ alkoxy, $Ar_1$, $C_2$-$C_6$ alkenyl, $C_2$-$C_6$ alkynyl, $C_3$-$C_7$ cycloalkyl, bicyclo[2.2.1]heptan-2-yl, 2,3-dihydro-1H-indenyl, 1,2,3,4-tetrahydronaphthyl, hydroxy; $C_2$-$C_6$ alkenyloxy that is unsubstituted or substituted by $Ar_2$; $C_2$-$C_6$ alkynyloxy; pyrimidyloxy; di($Ar_2$) methoxy, (1-$C_1$-$C_4$ alkyl-4-piperidinyl)oxy, $C_1$-$C_{10}$ alkoxy; or $C_1$-$C_{10}$ alkoxy that is substituted by halogen, hydroxy, $C_1$-$C_6$ alkyloxy, amino, mono- or di-($C_1$-$C_6$ alkyl)amino, trifluoromethyl, carboxy, $C_1$-$C_6$ alkoxycarbonyl, Ar.sub.1, $Ar_2$—O—, $Ar_2$—S—, $C_3$-$C_7$ cycloalkyl, 2,3-dihydro-1,4-benzodioxinyl, 1H-benzimidazolyl, $C_1$-$C_4$ alkyl-substituted 1H-benzimidazolyl, (1,1'-biphenyl)-4-yl or by 2,3-dihydro-2-oxo-1H-benzimidazolyl; and $R_3$ is hydrogen, nitro, amino, mono- or di-($C_1$-$C_6$ alkyl)amino, halogen, $C_1$-$C_6$ alkyl, hydroxy or $C_1$-$C_6$ alkoxy; wherein $Ar_1$ is phenyl, substituted phenyl, naphthyl, pyridyl, aminopyridyl, imidazolyl, triazolyl, thienyl, halothienyl, furanyl, $C_1$-$C_6$ alkylfuranyl, halofuranyl or thiazolyl; wherein $Ar_2$ is phenyl, substituted phenyl or pyridyl; and wherein "substituted phenyl" is phenyl that is substituted by up to 3 substituents in each case selected independently of one another from the group consisting of halogen, hydroxy, hydroxymethyl, trifluoromethyl, $C_1$-$C_6$ alkyl, $C_1$-$C_6$ alkoxy, $C_1$-$C_6$ alkoxycarbonyl, carboxy, formyl, hydroxyiminomethyl, cyano, amino, mono- and di-($C_1$-$C_6$ alkyl)amino and nitro.

Individual compounds from that group that may be given special mention are:
(1) 6-[(1H-imidazol-1-yl)-phenylmethyl]-1-methyl-1H-benzotriazole,
(2) 6-[(4-chlorophenyl)(1H-1,2,4-triazol-1-yl)methyl]-1-methyl-1H-benzotriazole.

(s) The compounds of Formula II as defined in European Patent Publication No. EP-A-250 198, especially
(1) 2-(4-chlorophenyl)-1,1-di(1,2,4-triazol-1-ylmethyl)ethanol,
(2) 2-(4-fluorophenyl)-1,1-di(1,2,4-triazol-1-ylmethyl)ethanol,
(3) 2-(2-fluoro-4-trifluoromethylphenyl)-1,1-di(1,2,4-triazol-1-ylmethyl)ethanol,
(4) 2-(2,4-dichlorophenyl)-1,1-di(1,2,4-triazol-1-ylmethyl)ethanol,
(5) 2-(4-chlorophenyl)-1,1-di(1,2,4-triazol-1-ylmethyl)-ethanol,
(6) 2-(4-fluorophenyl)-1,1-di(1,2,4-triazol-1-yl-methyl)ethanol.

(t) The compounds of Formula I as defined in European Patent Publication No. EP-A-281 283, especially
(1) (1R*2R*)-6-fluoro-2-(4-fluorophenyl)-1,2,3,4-tetrahydro-1-(1H-1,2,4-triazol-1-yl-methyl)naphthalene,
(2) (1R*,2R*)-6-fluoro-2-(4-fluorophenyl)-1,2,3,4-tetrahydro-1-(1H-imidazolylmethyl)-naphthalene,
(3) (1R*,2R*)- and (1R*,2S*)-2-(4-fluorophenyl)-1,2,3,4-tetrahydro-1-(1H-1,2,4-triazol-1-ylmethyl)naphthalene-6-carbonitrile,
(4) (1R*,2R*)- and (1R*,2S*)-2-(4-fluorophenyl)-1,2,3,4-tetrahydro-1-(1H-imidazolylmethyl)naphthalene-6-carbonitrile,
(5) (1R*,2R*)- and (1R*,2S*)-1,2,3,4-tetrahydro-1-(1H-1,2,4-triazol-1-ylmethyl)-naphthalene-2,6-dicarbonitrile,
(6) (1R*,2R*)- and (1R*,2S*)-1,2,3,4-tetrahydro-1-(1H-imidazol-1-ylmethyl)naphthalene-2,6-dicarbonitrile,
(7) (1R*,2S*)-2-(4-fluorophenyl)-1,2,3,4-tetrahydro-1-(5-methyl-1H-imidazolyl-methyl)naphthalene-6-carbonitrile.

(u) The compounds of Formula I as defined in European Patent Publication No. EP-A-296 749, especially
(1) 2,2'-[5-(1H-1,2,4-triazol-1-ylmethyl)-1,3-phenylene]di(2-methylpropiononitrile),
(2) 2,2'-[5-(imidazol-1-ylmethyl)-1,3-phenylene]di (2 methylpropiononitrile),
(3) 2-[3-(1-hydroxy-1-methylethyl)-5-(5H-1,2,4-triazol-1-ylmethyl)phenyl]-2-methylpropiononitrile,
(4) 2,2'-[5-dideuterio(1H-1,2,4-triazol-1-yl)methyl-1,3-phenylene]di(2-trideuteriomethyl-3,3,3-trideuteriopropiononitrile),
(5) 2,2'-[5-dideuterio(1H-1,2,4-triazol-1-yl)methyl-3-phenylene]di(2-methylpropiononitrile).

(v) The compounds of Formula I as defined in European Patent Publication No. EP-A-299 683, especially
(1) (Z)-a-(1,2,4-triazol-1-ylmethyl)stilbene-4,4'-dicarbonitrile,
(2) (Z)-4'-chloro-a-(1,2,4-triazol-1-ylmethyl)stilbene-4-carbonitrile,
(3) (Z)-a-(1,2,4-triazol-1-ylmethyl)-4'-(trifluoromethyl)stilbene-4-carbonitrile,
(4) (E)-.beta.-fluoro-a-(1,2,4-triazol-1-ylmethyl)stilbene-4,4'-dicarbonitrile,
(5) (Z)-4'-fluoro-a-(imidazol-1-ylmethyl)stilbene-4-carbonitrile,
(6) (Z)-2',4'-dichloro-a-(imidazol-1-ylmethyl)stilbene-4-carbonitrile,
(7) (Z)-4'-chloro-a-(imidazol-1-ylmethyl)stilbene-4-carbonitrile,
(8) (Z)-a-(imidazol-1-ylmethyl)stilbene-4,4'dicarbonitrile,
(9) (Z)-a-(5-methylimidazol-1-ylmethyl)stilbene-4,4'-dicarbonitrile,
(10) (Z)-2-[2-(4-cyanophenyl)-3-(1,2,4-triazol-1-yl)propenyl]pyridine-5-carbonitrile.

(w) The compounds of Formula I as defined in European Patent Publication No. EP-A-299 684, especially
(1) 2-(4-chlorobenzyl)-2-fluoro-1,3-di(1,2,4-triazol-1-yl)propane,
(2) 2-fluoro-2-(2-fluoro-4-chlorobenzyl)-1,3-di(1,2,4-triazol-1-yl)propane,
(3) 2-fluoro-2-(2-fluoro-4-trifluoromethylbenzyl)-1,3-di(1,2,4-triazol-1-yl)propane,
(4) 3-(4-chlorophenyl)-1-(1,2,4-triazol-1-yl)-2-(1,2,4-triazol-1-ylmethyl)butan-2-ol,
(5) 2-(4-chloro-a-fluorobenzyl)-1,3-di(1,2,4-triazol-1-yl)propan-2-ol,
(6) 2-(4-chlorobenzyl)-1,3-bis(1,2,4-triazol-1-yl)propane,
(7) 4-[2-(4-chlorophenyl)-1,3-di(1,2,4-triazol-1-ylmethyl)ethoxymethyl]-benzonitrile,
(8) 1-(4-fluorobenzyl)-2-(2-fluoro-4-trifluoromethylphenyl)-1,3-di(1,2,4-triazol-1-yl)-propan-2-ol,
(9) 2-(4-chlorophenyl)-1-(4-fluorophenoxy)-1,3-di(1,2,4-triazol-1-yl)propan-2-ol,
(10) 1-(4-cyanobenzyl)-2-(2,4-difluorophenyl)-1,3di(1,2,4-triazol-1-yl)propan-2-ol,
(11) 2-(4-chlorophenyl)-1-phenyl-1,3-di(1,2,4-triazol-1-yl)propan-2-ol.

(x) The compounds as defined in claim 1 of European Patent Publication No. EP-A-316 097, especially
(1) 1,1-dimethyl-8-(1H-1,2,4-triazol-1-ylmethyl)-2(1H)-naphtho[2,1-b]furanone,
(2) 1,2-dihydro1,1-dimethyl-2-oxo-8-(1H-1,2,4-triazol-1-ylmethyl)naphtho[2,1-b]-furan-7-carbonitrile,
(3) 1,2-dihydro-1,1-dimethyl-2-oxo-8-(1H-1,2,4-triazol-1-ylmethyl)naphtho[2,1-b]-furan-7-carboxamide,
(4) 1,2-dihydro-1,1-dimethyl-2-oxo-8-[di(1H-1,2,4-triazol-1-yl)methyl]naphtho[2,1-b]-furan-7-carbonitrile.

(y) The compounds of Formula I as defined in European Patent Publication No. EP-A-354 689, especially
(1) 4-[2-(4-cyanophenyl)-3-(1,2,4-triazol-1-yl)propyl]benzonitrile,
(2) 4-[1-(4-chlorobenzyl)-2-(1,2,4-triazol-1-yl)ethyl]benzonitrile,
(3) 4-[2-(1,2,4-triazol-1-yl)-1-(4-trifluoromethyl]benzyl)ethyl]benzonitrile,
(4) 4-[2-(1,2,4-triazol-1-yl)-1-(4-[trifluoromethoxy]benzyl)ethyl]benzonitrile.
(z) The compounds of formula (I) as defined in European Patent Publication No. EP-A-354 683, especially
(1) 6-[2-(4-cyanophenyl)-3-(1,2,4-triazol-1-yl)-propyl]nicotinonitrile,
(2) 4-[1-(1,2,4-triazol-1-yl-methyl)-2-(5-[trifluoromethyl]pyrid-2-yl)ethyl]benzonitrile.

Examples of steroidal aromatase inhibitors that may be mentioned are:
(aa) The compounds of Formula I as defined in European Patent Publication No. EP-A-181 287. These are especially the compounds of Formula I

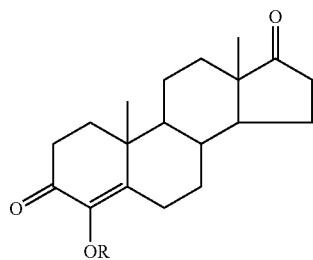

wherein R is hydrogen, acetyl, heptanoyl or benzoyl.

An individual compound from that group that may be given special mention is:
(1) 4-hydroxy-4-androstene-3,17-dione.
(ab) The compounds as defined in the claims of U.S. Pat. No. 4,322,416, especially 10-(2-propynyl)-oestr-4-ene-3,17-dione.
(ac) The compounds as defined in the claims of German Patent Application No. DE-A-3 622 841, especially 6-methyleneandrosta-1,4-diene-3,17-dione.
(ad) The compounds as defined in the claims of Published British Patent Application No. GB-A-2 171 100, especially 4-amino-androsta-1,4,6-triene-3,17-dione.
(ae) The compound androsta-1,4,6-triene-3,17-dione.

The content of the patent applications mentioned under (a) to (z) and (aa) to (ad), especially the subgroups of compounds disclosed therein and the individual compounds disclosed therein as examples, are incorporated by reference into the disclosure of the present application.

The general terms used hereinbefore and hereinafter to define the compounds have the following meanings:

Organic radicals designated by the term "lower" contain up to and including 7, and preferably up to and including 4, carbon atoms.

Acyl is especially a lower alkanoyl.

Aryl is, for example, phenyl or 1- or 2-naphthyl, each of which is unsubstituted or substituted by lower alkyl, hydroxy, lower alkoxy, lower alkanoyloxy, amino, lower alkylamino, di-lower alkylamino, lower alkanoylamino or by halogen.

Pharmaceutically acceptable salts of the above-mentioned compounds are, for example, pharmaceutically acceptable acid addition salts or pharmaceutically acceptable metal or ammonium salts.

Pharmaceutically acceptable acid addition salts are especially those with suitable inorganic or organic acids, for example strong mineral acids, such as hydrochloric acid, sulfuric acid or phosphoric acid, or organic acids, especially aliphatic or aromatic carboxylic or sulfonic acids, for example formic, acetic, propionic, succinic, glycolic, lactic, hydroxysuccinic, tartaric, citric, maleic, fumaric, hydroxymaleic, pyruvic, phenylacetic, benzoic, 4-aminobenzoic, anthranilic, 4-hydroxybenzoic, salicylic, 4-aminosalicylic, pamoic, gluconic, nicotinic, methanesulfonic, ethanesulfonic, halobenzenesulfonic, p-toluenesulfonic, naphthalenesulfonic, sulfanilic or cyclohexylsulfamic acid; or with other acidic organic substances, for example ascorbic acid.

Pharmaceutically acceptable salts may also be formed, for example, with amino acids, such as arginine or lysine. Compounds containing acid groups, for example a free carboxy or sulfo group, can also form pharmaceutically acceptable metal or ammonium salts, such as alkali metal or alkaline earth metal salts, for example sodium, potassium, magnesium or calcium salts, or ammonium salts derived from ammonia or suitable organic amines. Also under consideration are especially aliphatic, cycloaliphatic, cycloaliphatic-aliphatic or araliphatic primary, secondary or tertiary mono-, di- or polyamines, such as lower alkylamines, for example di- or triethylamine, hydroxy-lower alkylamines, for example 2-hydroxyethylamine, bis(2-hydroxyethyl)amine or tris(2-hydroxyethyl)amine, basic aliphatic esters or carboxylic acids, for example 4-aminobenzoic acid 2-diethylaminoethyl ester, lower alkyleneamines, for example 1-ethylpiperidine, cycloalkylamines, for example dicyclohexylamine, benzylamines, for example N,N'-dibenzylethylenediamine; also heterocyclic bases, for example of the pyridine type, for example pyridine, collidine or quinoline. If several acidic or basic groups are present, mono- or poly-salts can be formed. Compounds according to the invention having an acidic and a basic group may also be in the form of internal salts, i.e., in the form of zwitterions and another part of the molecule in the form of a normal salt.

In the case of the above-mentioned individual compounds the pharmaceutically acceptable salts are included in each case insofar as the individual compound is capable of salt formation.

The compounds listed, including the individual compounds mentioned, both in free form and in salt form, may also be in the form of hydrates, or their crystals may include, for example, the solvent used for crystallisation. The present invention relates also to all those forms.

Many of the above-mentioned compounds, including the individual compounds mentioned, contain at least one asymmetric carbon atom. They can, therefore, occur in the form of R- or S-enantiomers and as enantiomeric mixtures thereof, for example in the form of a racemate. The present invention relates to the use of all those forms and to the use of all further isomers, and of mixtures of at least 2 isomers, for example mixtures of diastereoisomers or enantiomers which can occur when there are one or more further asymmetric centres in the molecule. Also included are, for example, all geometric isomers, for example cis- and trans-isomers, that can occur when the compounds contain one or more double bonds.

In another embodiment of the present invention, pharmaceutical compositions provide the AI compound in a dosage form with suitable carriers, fillers and/or excipients. Pharmaceutical composition that can be prepared according to the invention are compositions for enteral, such as peroral or rectal administration, also for transdermal or sublingual administration, and for parenteral, for example intravenous, subcutaneous and intramuscular, administration. Suitable unit dose forms, especially for peroral and/or sublingual administration, for example dragees, tablets or capsules, comprise preferably from approximately 0.01 mg to approximately 20 mg, especially from approximately 0.1 mg to approximately 10 mg, of one or more of the above-mentioned compounds, or of pharmaceutically acceptable salts thereof, together with pharmaceutically acceptable carriers. The particularly preferred form of administration is oral.

The proportion of active ingredient in such pharmaceutical compositions is generally from approximately 0.001% to approximately 60%, preferably from approximately 0.1% to approximately 20%.

Suitable excipients for pharmaceutical compositions for oral administration are especially fillers, such as sugars, for example lactose, saccharose, mannitol or sorbitol, cellulose preparations and/or calcium phosphates, for example tricalcium phosphate or calcium hydrogen phosphate, and binders, such as starches, for example corn, wheat, rice or potato starch, gelatin, tragacanth, methylcellulose and/or hydroxypropylcellulose, disintegrators, such as the above-mentioned starches, also carboxymethyl starch, cross-linked polyvinylpyrrolidone, agar, alginic acid or a salt thereof, such as sodium alginate, and/or cellulose, for example in the form of crystals, especially in the form of microcrystals, and/or flow regulators and lubricants, for example silicic acid, talc, stearic acid or salts thereof, such as magnesium or calcium stearate, cellulose and/or polyethylene glycol.

Dragee cores can be provided with suitable, optionally enteric, coatings, there being used inter alia concentrated sugar solutions which may comprise gum arabic, talc, polyvinylpyrrolidone, polyethylene glycol and/or titanium dioxide, or coating solutions in suitable solvents or solvent mixtures, or, for the preparation of enteric coatings, solutions of suitable cellulose preparations, such as acetylcellulose phthalate or hydroxypropylmethylcellulose phthalate.

Other orally administrable pharmaceutical compositions are dry-filled capsules consisting of gelatin, and also soft sealed capsules consisting of gelatin and a plasticiser, such as glycerol or sorbitol. The dry-filled capsules may contain the active ingredient in the form of granules, for example in admixture with fillers, such as lactose, binders, such as starches, and/or glidants, such as talc or magnesium stearate, and, if desired, stabilisers. In soft capsules, the active ingredient is preferably dissolved or suspended in suitable oily excipients, such as fatty oils, paraffin oil or liquid polyethylene glycols, to which stabilisers and/or anti-bacterial agents may also be added. There may also be used capsules that are easily bitten through, in order to achieve by means of the sublingual ingestion of the active ingredient that takes place as rapid an action as possible.

Suitable rectally or transvaginally administrable pharmaceutical compositions are, for example, suppositories that consist of a combination of the active ingredient with a suppository base. Suitable suppository bases are, for example, natural or synthetic triglycerides, paraffin hydrocarbons, polyethylene glycols or higher alkanols. There may also be used gelatin rectal capsules, which contain a combination of the active ingredient with a base material. Suitable base materials are, for example, liquid triglycerides, polyethylene glycols or paraffin hydrocarbons.

Suitable formulations for transdermal administration comprise the active ingredient together with a carrier. Advantageous carriers include absorbable pharmacologically acceptable solvents that serve to facilitate the passage through the skin of the host. Transdermal systems are usually in the form of a bandage that comprises a support, a supply container containing the active ingredient, if necessary together with carriers, optionally a separating device that releases the active ingredient onto the skin of the host at a controlled and established rate over a relatively long period of time, and means for securing the system to the skin.

Suitable for parenteral administration are especially aqueous solutions of an active ingredient in water-soluble form, for example in the form of a water-soluble salt, and also suspensions of active ingredient, such as corresponding oily injection suspensions, there being used suitable lipophilic solvents or vehicles, such as fatty oils, for example sesame oil, or synthetic fatty acid esters, for example ethyl oleate, or triglycerides, or aqueous injection suspensions that comprise viscosity-increasing substances, for example sodium carboxymethylcellulose, sorbitol and/or dextran, and, optionally, stabilisers.

Dyes or pigments may be added to the pharmaceutical compositions, especially to the tablets or dragee coatings, for example for identification purposes or to indicate different doses of active ingredient.

The pharmaceutical compositions of the present invention can be prepared in a manner known per se, for example by means of conventional mixing, granulating, confectioning, dissolving or lyophilising processes. For example, pharmaceutical compositions for oral administration can be obtained by combining the active ingredient with solid carriers, optionally granulating a resulting mixture, and processing the mixture or granules, if desired or necessary after the addition of suitable excipients, to form tablets or dragee cores.

The success of aromatase inhibitors in preventing the establishment and maintenance of early pregnancy in ectopic pregnancy would make this class of medication and the use of aromatase inhibition a valid novel approach for medical termination of pregnancy. This would be of great benefit especially for women with significant medical problems contraindicating surgical termination of pregnancy or the use of the currently available methods of medical termination of pregnancy. Those women might benefit from the wide safety profile of such class of medications.

Aromatase inhibitors have not been used in women of the reproductive age group until recently. We have found that estrogen levels following induction or augmentation of ovulation with aromatase inhibitors were significantly lower (especially serum E2 concentration/mature follicle) when compared with conventional stimulation protocols.

Typically, the amount of aromatase inhibitor for preventing the achievement and/or establishment and/or maintenance of pregnancy in females exposed to unprotected sexual encounter that may lead to pregnancy may be selected from amounts that lower estrogen levels resulting in disruption of endometrial integrity leading to shedding of the endometrium and induced menstruation or at least destroying the integrity of the endometrial structure that will be unfavorable for the implantation of a fertilized oocyte or maintenance of early pregnancy. Medical termination of pregnancy can result, preferably from 1 to 10 daily doses of the aromatase inhibitor with administration starting on any of days 1 to 10 after exposure to unprotected intercourse, for 1-10 days. Most preferably the daily doses of the aromatase inhibitor comprise five daily doses.

Although the invention has been described in terms of specific embodiments and applications, persons skilled in the art may, in light of this teaching, generate additional embodiments without exceeding the scope or departing from the spirit of the claimed invention. Accordingly, it is to be understood that the drawing and description in this disclosure are proffered to facilitate comprehension of the invention and should not be construed to limit the scope thereof.

What is claimed is:

1. A method of preventing the establishment and/or continuation of an ectopic pregnancy in a patient, the method consisting essentially of the steps of:
   (1) diagnosing ectopic pregnancy; and
   (2) administering to the patient one or more doses of a pharmaceutical composition having at least one aromatase inhibitor as the active ingredient, the at least one aromatase inhibitor being administered in an amount effective to induce ectopic pregnancy atrophy and/or destruction.

2. The method of claim 1 further including the step of administering the at least one aromatase inhibitor before, in conjunction with, or following, surgical management as an adjuvant.

3. The method of claim 2 wherein surgical management is laparoscopy.

4. The method of claim 1 wherein from 1 to 10 daily doses of the aromatase inhibitor are administered.

5. The method of claim 4 wherein about 5 daily doses are administered.

6. The method of claim 1 wherein the aromatase inhibitor has a steroidal or non-steroidal chemical structure.

7. The method of claim 6 wherein the aromatase inhibitor is selected from non-steroidal and reversible aromatase inhibitors.

8. The method of claim 1 wherein the aromatase inhibitor is a third generation inhibitor selected from the group consisting of anastrozole, letrozole, vorozole and exemestane.

9. The method of claim 8 wherein the aromatase inhibitor is letrozole and is administered in a daily dose of from about 2.5 mg to about 30 mg.

10. The method of claim 8 wherein the aromatase inhibitor is anastrozole and is administered in a daily dose of from about 1 mg to about 30 mg.

11. The method of claim 8 wherein the aromatase inhibitor is vorozole and is administered in a daily dose of from about 4 mg to about 30 mg.

12. The method of claim 8 wherein the aromatase inhibitor is exemestane and is administered in a daily dose of from about 25 mg to about 2000 mg.

13. The method of claim 1 wherein the aromatase inhibitor is selected from aromatase inhibitors having a half-life of about 8 hours to about 4 days.

14. The method of claim 13 wherein the aromatase inhibitor is selected from aromatase inhibitors having a half-life of about 2 days.

15. The method of claim 1 wherein the aromatase inhibitor is administered orally.

16. The method of claim 1 wherein the amount of aromatase inhibitor is selected from amounts that lower estrogen levels resulting in disruption of endometrial integrity leading to shedding of the endometrium and induced menstruation or that destroy the integrity of the endometrial structure.

* * * * *